(12) United States Patent
Smith et al.

(10) Patent No.: US 8,135,201 B2
(45) Date of Patent: Mar. 13, 2012

(54) IMAGE PROCESSING SYSTEM FOR USE WITH A PATIENT POSITIONING DEVICE

(75) Inventors: Norman Ronald Smith, London (GB); Ivan Daniel Meir, Potters Bar (GB); Gideon Matthew Hale, Basingstoke (GB); Robert Edward Howe, Spring Hill (AU)

(73) Assignee: Vision RT Limited, London (GB)

( * ) Notice: Subject to any disclaimer, the term of this patent is extended or adjusted under 35 U.S.C. 154(b) by 0 days.

(21) Appl. No.: 12/929,228

(22) Filed: Jan. 10, 2011

(65) Prior Publication Data
US 2011/0178783 A1 Jul. 21, 2011

Related U.S. Application Data

(63) Continuation of application No. 10/516,400, filed on Jun. 7, 2006, now Pat. No. 7,889,906.

(30) Foreign Application Priority Data

Jul. 8, 2002 (GB) .................................. 0125764.2

(51) Int. Cl.
*G06K 9/00* (2006.01)
*G06K 9/32* (2006.01)
*G06F 7/60* (2006.01)

(52) U.S. Cl. .............................. 382/132; 382/294; 703/2

(58) Field of Classification Search ................... 382/100, 382/128–134, 154, 289–297; 356/455–456; 345/418–419, 424; 708/1–7, 100; 702/1–2; 703/1–2; 128/922; 600/1–9, 425, 407; 378/4, 378/62, 98.11, 98.12, 15–20
See application file for complete search history.

(56) References Cited

U.S. PATENT DOCUMENTS

| 5,446,548 | A | 8/1995 | Gerig et al. |
| 5,447,154 | A | 9/1995 | Cinquin et al. |
| 5,946,425 | A | 8/1999 | Bove, Jr. et al. |
| 5,954,647 | A | 9/1999 | Bova et al. |
| 6,154,518 | A | 11/2000 | Gupta |
| 7,065,242 | B2 * | 6/2006 | Petrov et al. .................. 382/154 |

(Continued)

FOREIGN PATENT DOCUMENTS

| GB | 2355789 | 5/2001 |
| JP | A-2001-229388 | 2/2000 |
| WO | WO 02/061680 | 8/2002 |

OTHER PUBLICATIONS

Milliken B D et al. "Performance of a video-image-subtraction-based patient positioning system," International Journal of Radiation Oncology Biology Physics, Jul. 1997, pp. 855-866, vol. 38, No. 4, Elsevier for America Soc. Therapeutic Radiol. & Oncol, USA.

(Continued)

*Primary Examiner* — Samir Ahmed
*Assistant Examiner* — Mehdi Rashidian
(74) *Attorney, Agent, or Firm* — Oliff & Berridge, PLC

(57) ABSTRACT

Three camera rigs are connected by wiring to a computer. The computer is also connected to a treatment apparatus. A mechanical couch is provided as part of the treatment apparatus such that under the control of the computer the relative positions of the mechanical couch and the treatment apparatus may be varied. The camera rigs obtain video images of a patient lying on the mechanical couch the computer processes these images to generate a three-dimensional model of the surface of the patient which is utilized to position the patient relative to the treatment apparatus.

6 Claims, 17 Drawing Sheets

U.S. PATENT DOCUMENTS

| | | | |
|---|---|---|---|
| 7,693,563 B2* | 4/2010 | Suresh et al. | 600/407 |
| 7,706,600 B2* | 4/2010 | Kreeger et al. | 382/154 |
| 7,889,906 B2* | 2/2011 | Smith et al. | 382/132 |
| 2002/0044682 A1 | 4/2002 | Weil et al. | |
| 2002/0050988 A1* | 5/2002 | Petrov et al. | 345/418 |
| 2004/0153128 A1* | 8/2004 | Suresh et al. | 607/14 |
| 2007/0003131 A1* | 1/2007 | Kaufman | 382/154 |
| 2007/0014452 A1* | 1/2007 | Suresh et al. | 382/128 |

OTHER PUBLICATIONS

Best et al., "A Method for Registration of 3-D Shapes," IEEE Transactions on Pattern Analysis and Machine Intelligence, pp. 239-256, vol. 14, No. 2, Feb. 1992.

Verhey, Immobilizing and Positioning Patients for Radiotherapy, Seminars in Radiation Oncology, Apr. 1995, pp. 100-144, vol. 5, No. 2.

Lam et al., "Automated determination of patient setup errors in radiation therapy using spherical radio-opaque markers" Med. Phys., Jul./Aug. 1983, pp. 21-27, vol. 20, No. 4.

Tsai, "A Versatile Camera Calibration Technique for High-Accuracy 3D Machine Vision Metrology Using Off-the-Shelf TV Cameras and Lenses" IEEE Journal of Robotics and Automation, Aug. 1987, vol. RA-3, No. 4.

Graham et al., "Dynamic Surface Matching for Patient Positioning in Radiotherapy," North Western Medical Physics, IEEE 1998, pp. 16-24, Christie Hospital, Manchester, UK.

* cited by examiner

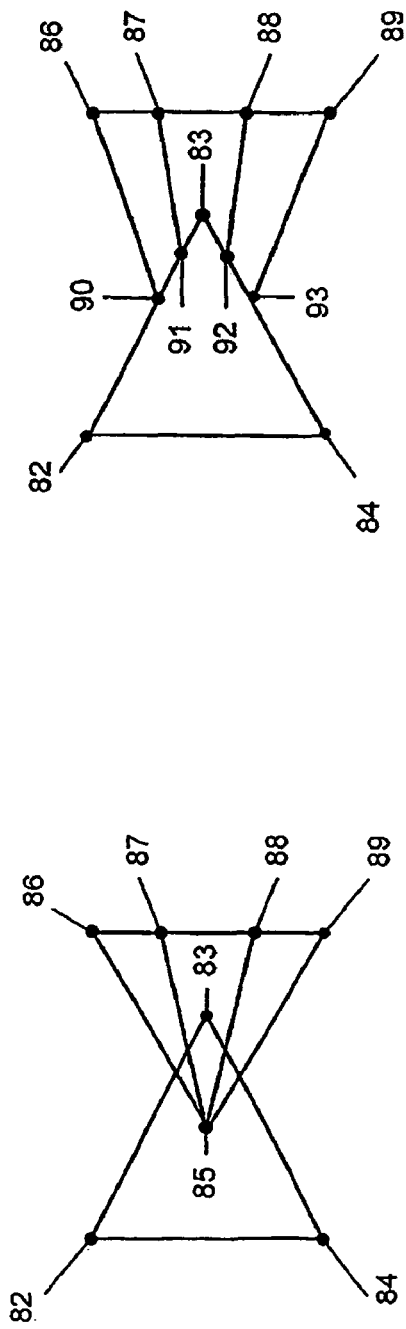
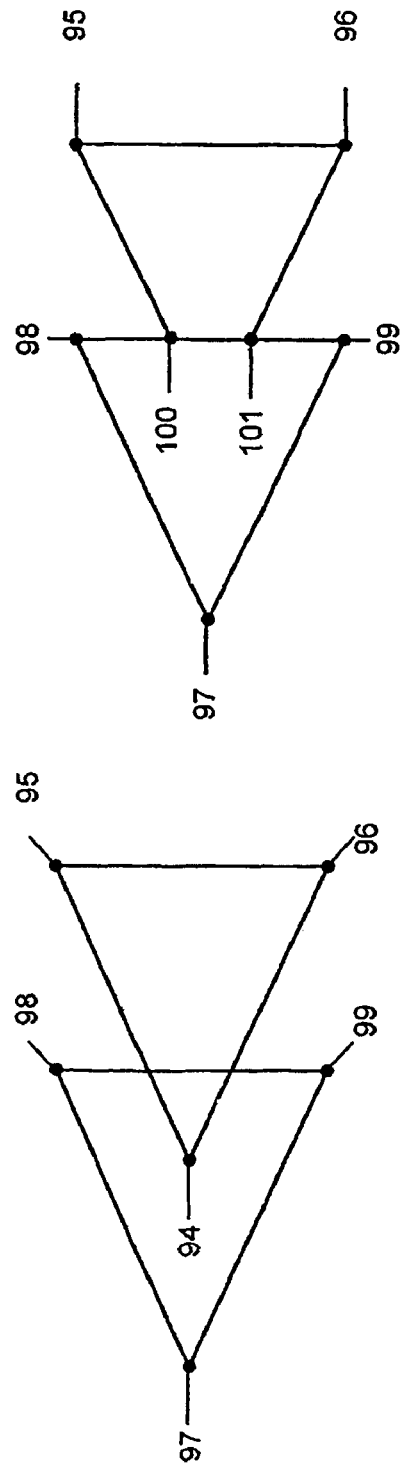
FIG. 12A
FIG. 12B
FIG. 11A
FIG. 11B

US 8,135,201 B2

IMAGE PROCESSING SYSTEM FOR USE WITH A PATIENT POSITIONING DEVICE

This is a Continuation of application Ser. No. 10/516,400 filed Jun. 7, 2006, which in turn is a National Stage of PCT/GB2003/002955, filed on Jul. 8, 2003, and which claims priority to British Application No. 0125764.2 filed Jul. 8, 2002 in the United Kingdom. The disclosure of the prior applications is hereby incorporated by reference herein in its entirety.

The present invention relates to image processing. More particularly, embodiments of the present invention relate to image processing systems for use with patient positioning devices.

One application of the present invention is in the field of radiotherapy. Radiotherapy consists of projecting onto a predetermined region of a patient's body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

To this end, radiotherapy usually takes place in two stages. In an initial planning stage the patient's body is scanned using a 2-D x-ray simulator or a CT simulator, or by Magnetic Resonance Imaging (MRI) to visualise the target site and any obstacles. The course of therapy is then planned using the images obtained from the x-ray scanner or using the MRI images. Subsequently in a treatment stage a patient is irradiated in accordance with the course of treatment planned during the planning stage.

A fundamental problem with radiotherapy is the need to position the patient in the same position, when obtaining diagnostic images and each of the subsequent times when radiation is applied to the patient's body. Present systems for positioning patients include various forms of systems for placing markers on the patient to enable the patient to be realigned for different applications of therapy. Thus for example U.S. Pat. No. 5,954,647 discloses the use of a specially moulded bite plate on which LED's are placed to enable the head of an individual to be orientated in the same position in which diagnostic images are obtained. Similarly U.S. Pat. No. 5,446,548 describes another positioning and monitoring system. The system of U.S. Pat. No. 5,446,548 involves the fixing of infra-red reflective markers on parts of a patient's body.

Although known systems involving the tracking of markers fixed relative to the patient enable the patient's positioning to be monitored, it is desirable to be able to determine the patient's position more accurately to increase the effectiveness of treatment. Further, it is desirable to provide a positioning system which minimises the extra time required and the inco-varience to a patient arising from placing or fixing markers and thus reduces the stresses placed upon the patient during treatment.

In accordance with one aspect of the present invention there is provided a patient positioning system in which a three-dimensional model of the surface of a patient is generated utilising a number of stereoscopic video images of the patient. The video images are processed to generate the three dimensional model which is rapidly updated to account for changes in the position of the patient.

In order to enable the surface model of a patient to be updated as rapidly as possible a number of techniques are utilised. In accordance with one aspect there is provided an image processing method comprising the steps of:
  obtaining stereoscopic images of an individual;
  generating a surface model of said individual utilising said stereoscopic images;
  receiving further stereoscopic images of said individual and generating a further model of said individual from said further stereoscopic images and said previous model of said individual.

In accordance with a further aspect of the present invention there is provided a method of image processing comprising the steps of:
  obtaining a first and a second image of an individual from a first and a second view point;
  identifying within said first and said second images, portions of said images corresponding to the same points on the surface of said individual; and
  for said points on said surface of said individual, determining the orientation of the surface of said individual at said points relative to said view points, wherein said determination of said orientations relative to said view points comprises:
  determining the orientation of a point on the surface of said individual;
  for adjacent points on the surface of said individual for which said orientation has not been determined, determining whether said determined orientation for said point is a better estimate of the orientation of said adjacent points than a current estimate of orientation for said adjacent points; and
  if said determined orientation is a better estimate than said current estimate, updating said current estimate for said adjacent points; and
  determining said orientation for said adjacent points utilising the best estimate of said orientation determined from said orientations for adjacent points.

Further aspects and embodiments of the present invention will become apparent with reference to the following description and accompanying drawings in which.

Figure 1:
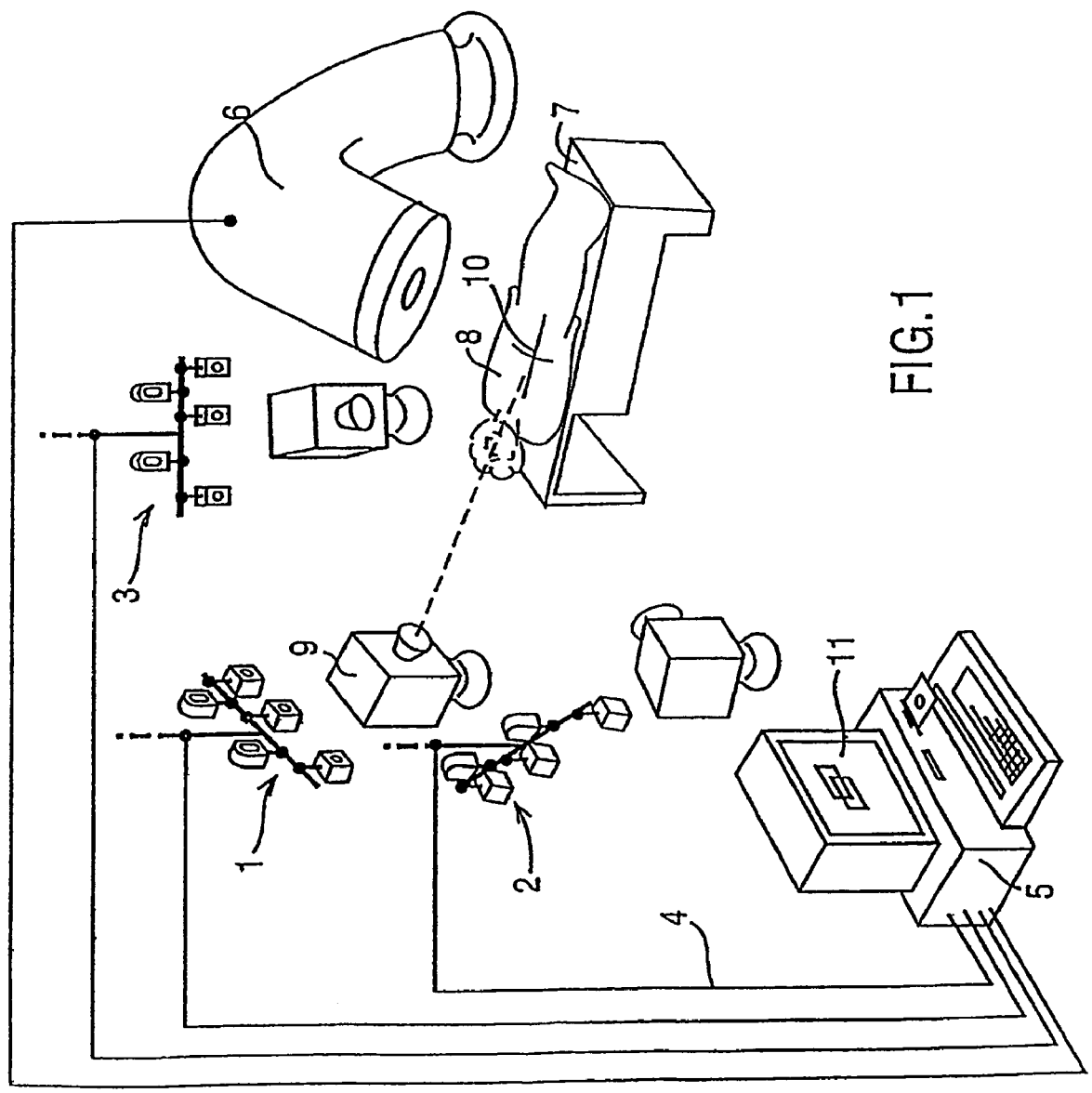
FIG. 1 is a schematic diagram of a patient positioning system in accordance with a first embodiment of the present invention.
Figure 3:
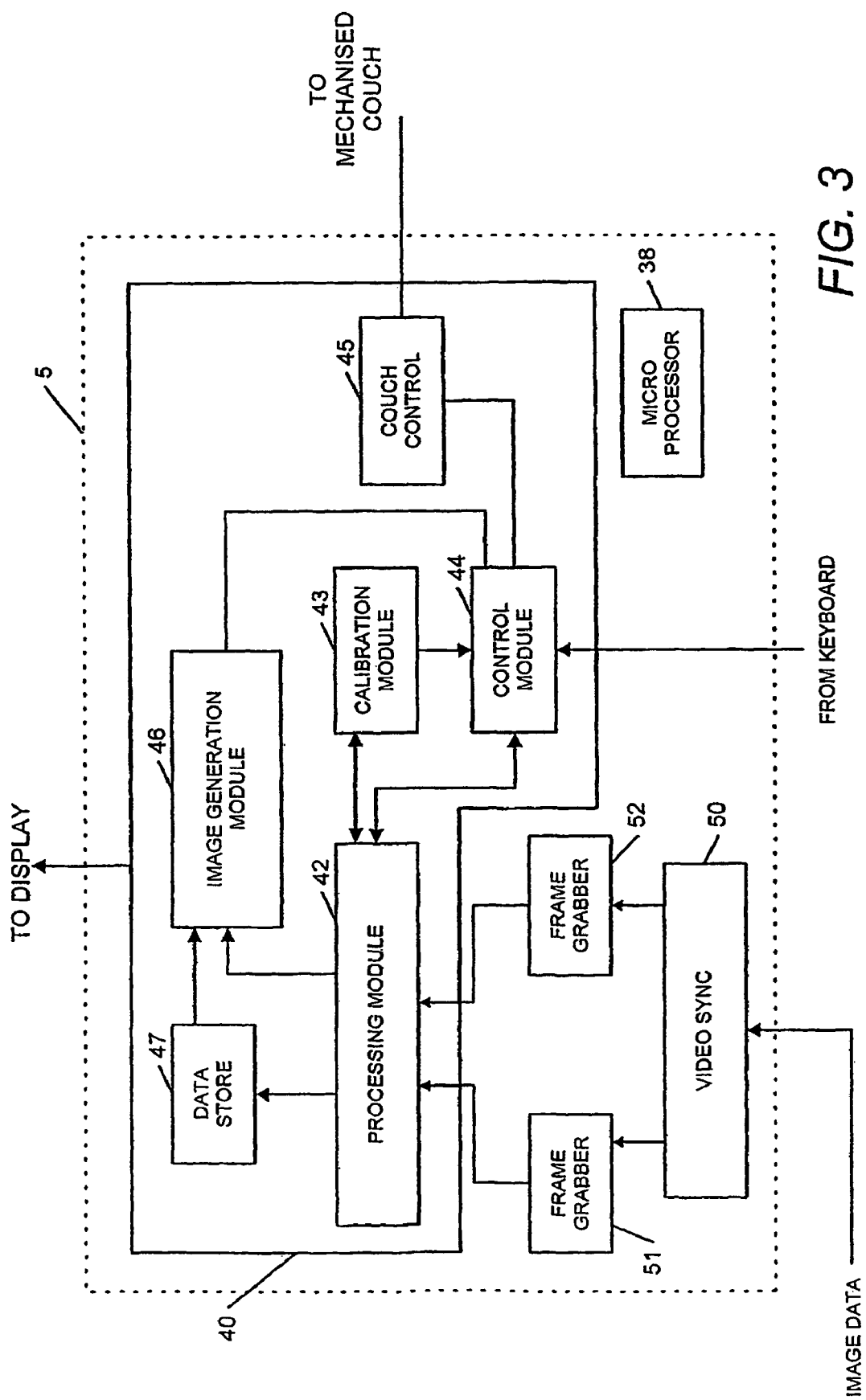
FIG. 3 is a block diagram of the computer of the patient positioning system of FIG. 1.
Figure 10A:
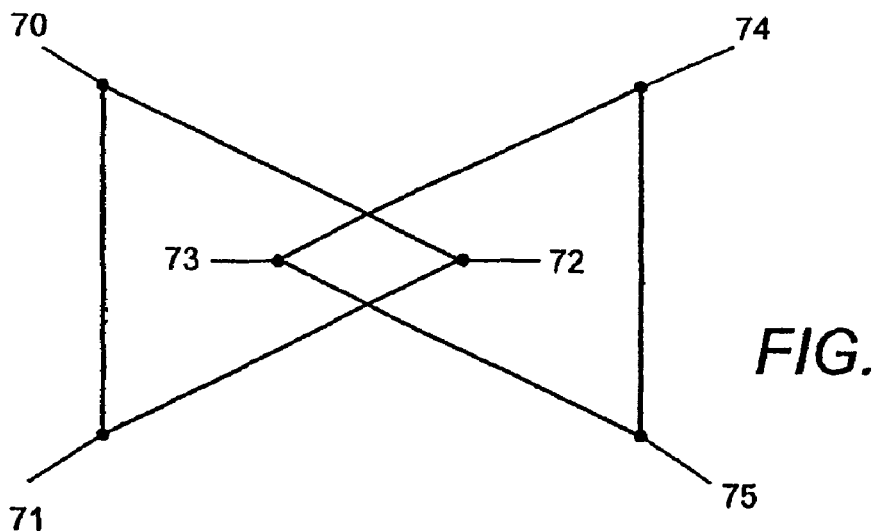
Figure 13:
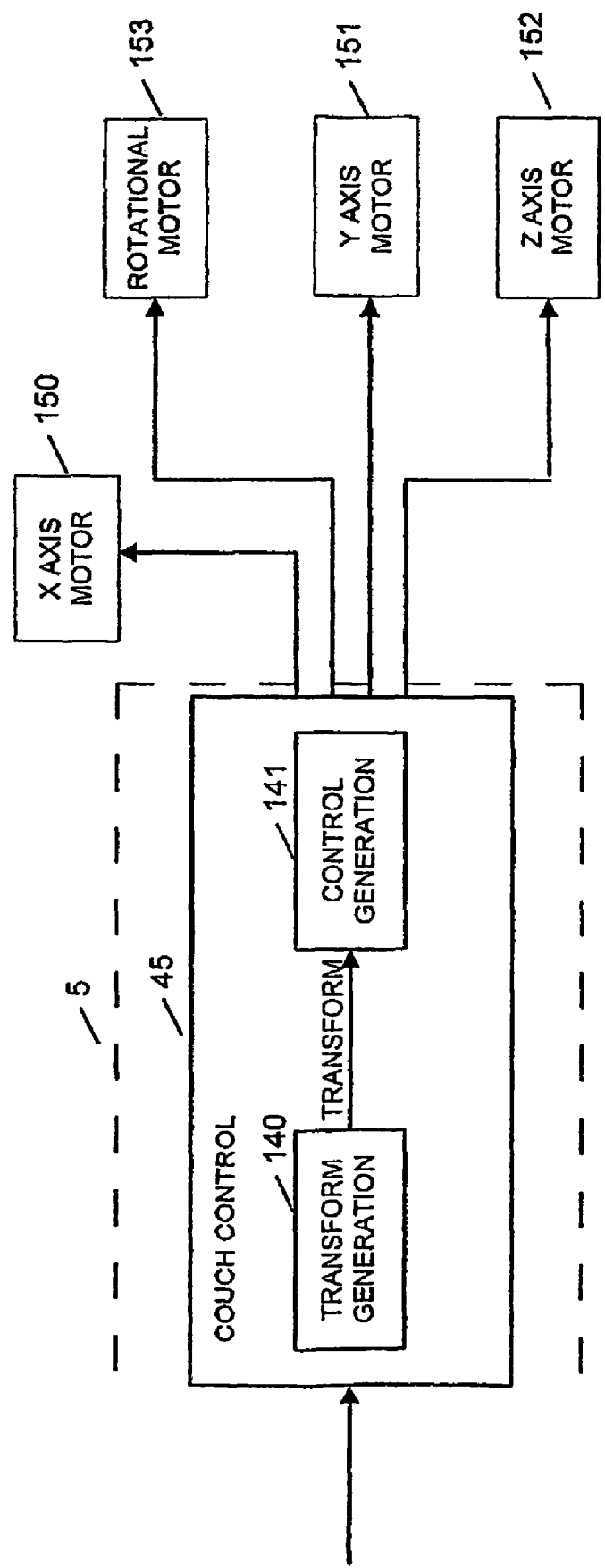
Figure 14:
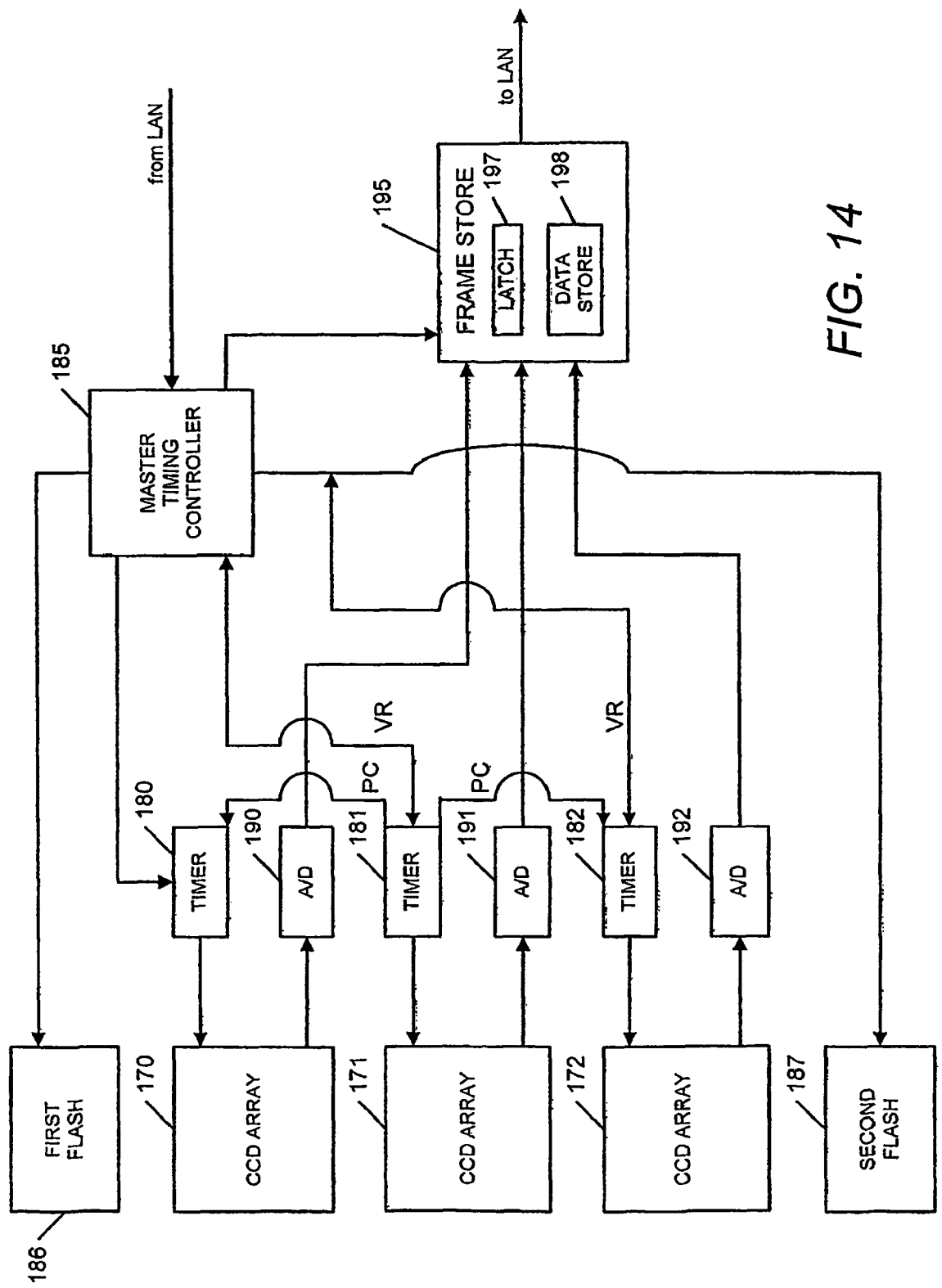
Figure 15:
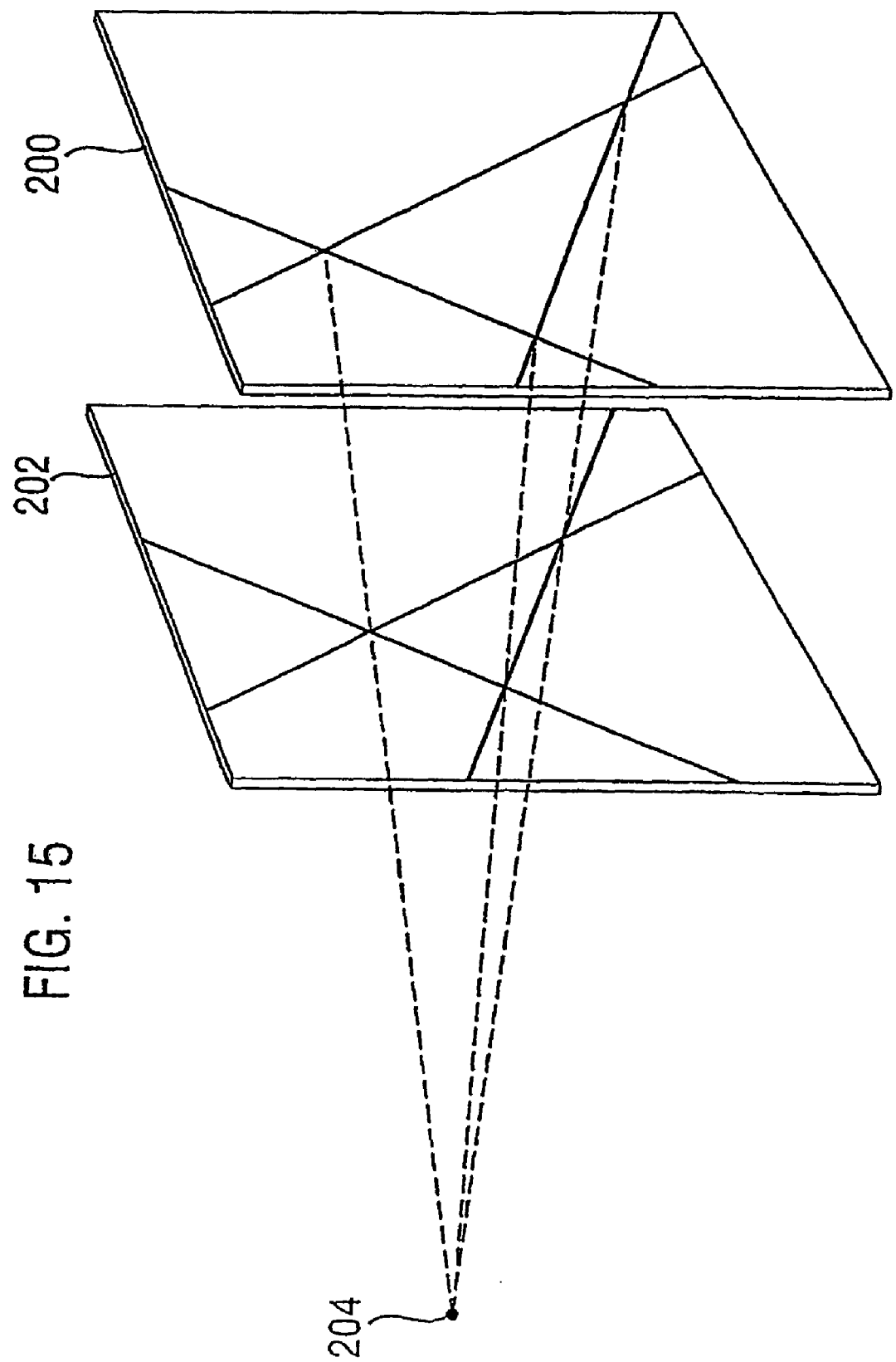

FIGS. 10A, B and C are schematic illustrations of the processing by the computer of FIG. 3 of a pair of overlapping triangles from different surfaces to merge to the two surfaces;

FIGS. 11A-E are schematic illustrations of five further types of overlap between the edges of two surfaces;

FIGS. 12A-E are schematic illustrations of the surfaces of FIGS. 11A-E after processing by the computer of FIG. 3;

FIG. 13 is a schematic illustration of the control system for varying the position of the mechanical couch of the patient positioning system of FIG. 1;

FIG. 14 is a schematic block diagram of a camera for use in a second embodiment of the present invention; and FIG. 15 is a schematic illustration for explaining a method of calibration.

FIRST EMBODIMENT

FIG. 1 is a schematic diagram of a patient positioning system in accordance with a first embodiment of the present invention. In accordance with this embodiment, there is provided a set of three camera rigs 1, 2, 3 that are connected by wiring 4 to a computer 5. The computer 5 is also connected to treatment apparatus 6 such as a linear accelerator for applying radiotherapy or an x-ray simulator for planning radiotherapy. A mechanical couch 7 is provided as part of the treatment apparatus 6 upon which a patient 8 lies during treatment. The treatment apparatus 6 and the mechanical couch 7 are arranged such that under the control of the computer 5 the relative positions of the mechanical couch 7 and the treatment apparatus 6 may be varied, laterally, vertically, longitudinally and rotationally. Also provided as part of the system is a laser projection apparatus 9 which is arranged to project three laser cross hairs 10 onto the body of a patient 8 lying on the mechanical couch 7 where the three laser cross hairs 10 are such to identify the focussing point of the radiation generated by the treatment apparatus 6.

In use, the cameras of the camera rigs 1, 2, 3 obtain video images of a patient 8 lying on the mechanical couch 7. These video images are passed via the wiring 4 to the computer 5. The computer 5 then processes the images in accordance with the present invention to generate a three-dimensional model of the surface of the patient, which is displayed on the screen 11 of the computer 5. The three-dimensional model of the patient is then continually updated utilising the stream of video images obtained from the cameras of the camera rigs 1, 2, 3. The three-dimensional models of the surface of a patient 8 are also utilised by the computer 5 to control the treatment apparatus 6 to position the mechanical couch 7 relative to the treatment apparatus 6 in a consistent manner throughout the course of a treatment.

Prior to describing in detail the image processing algorithms utilised to generate and vary the three-dimensional model of the surface of a patient 8, the structure of the camera rigs 1, 2, 3 will first be described in detail with reference to FIG. 2.

Figure 2:
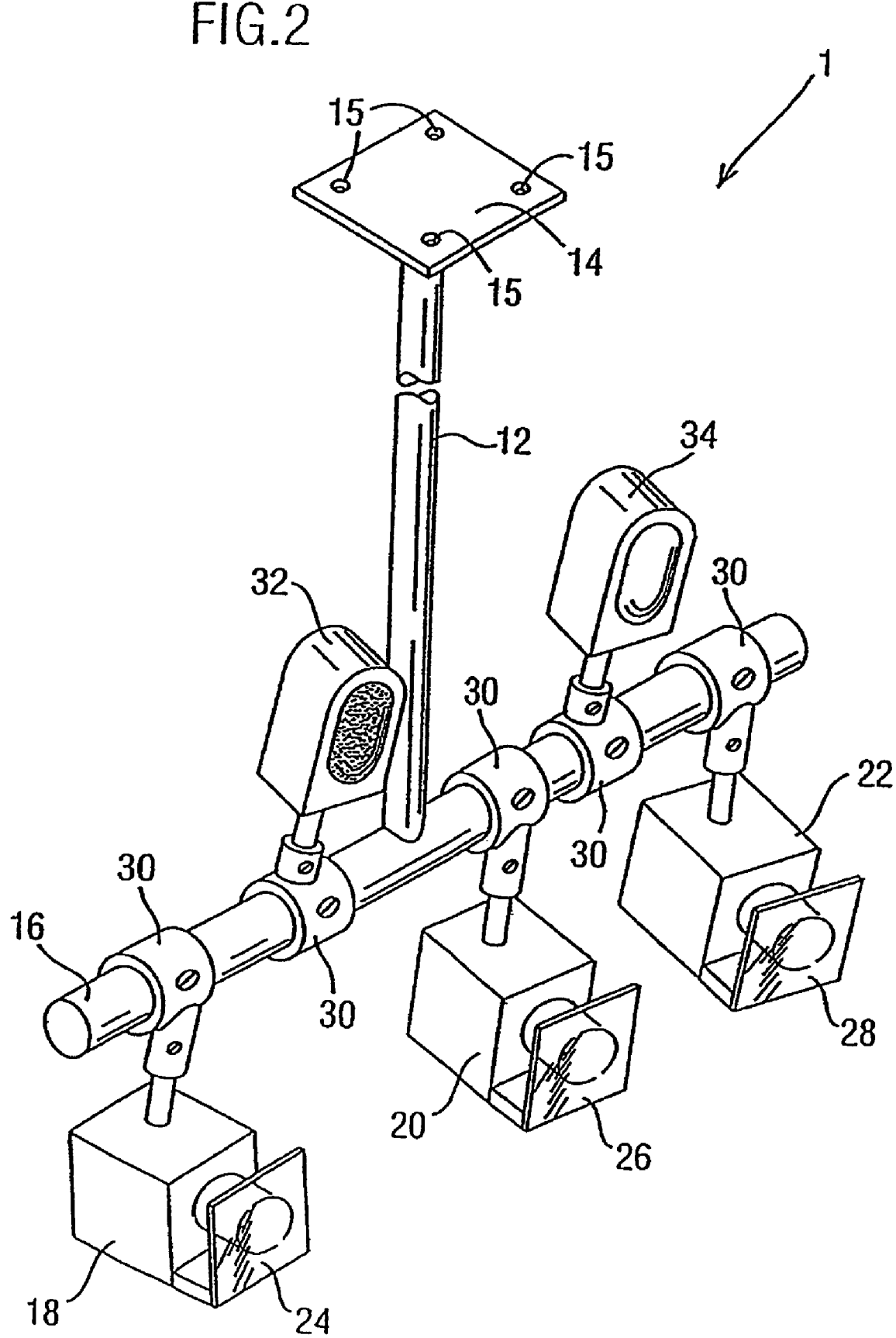
FIG. 2 is a perspective view of a camera rig of the patient positioning system of FIG. 1.

FIG. 2 is a schematic illustration of one of the set of camera rigs 1, 2, 3 of this embodiment of the present invention. All of the camera rigs 1, 2, 3 in this embodiment are identical to the others with the three camera rigs 1, 2, 3 being arranged with one either side of the mechanical couch 7 and one at the head of the mechanical couch 7. The arrangement of cameras of the rigs 1, 2, 3 are such that all the cameras of the camera rigs view substantially the same portion of the patient immediately beneath the treatment apparatus 6 so that a complete model of that portion of the patient 8 can be generated.

The camera rigs 1, 2, 3 each comprise a T-bar 12 which is suspended from the roof of the room within which the treatment apparatus 6 is provided. To this end a base plate is provided at the top of the T-bar 12 with the main body of the T-bar 12 extending down from the centre of this base plate. Provided in each of the corners of the base plate 14 are fixing holes 15 through which bolts pass to fix the T-bar 12 in position in the room containing the treatment apparatus 6.

Provided at the opposite end of the T-bar 12 to the base plate 14 attached to the horizontal cross bar 16 forming the T-section of the T-bar are three cameras 18,22,24. These cameras 18,22,24 are arranged along the cross bar 16, and in order from left to right along the cross bar 16 are a first geometry camera 18, a texture camera 20 and a second geometry camera 22. The cameras 18, 20, 22 each comprise monochrome analogue video cameras such as the Pulnix PE100.

Provided in front of the lenses of each of the cameras is are filters 24, 26, 28. The filters on the two geometry cameras 18, 22 are arranged to prevent the geometry cameras 18,24 from receiving light having a wavelength below 570 nm. The filter 26 in front of the lens of the texture camera 20 comprises a filter preventing the texture camera 20 from receiving light with a wavelength greater than 540 nm.

Each of the cameras 18, 20, 22 is attached to the horizontal bar 16 of the T-bar 12 by a clamp 30 which attaches the cameras 18, 20, 22 to the horizontal cross bar 16 of the T-bar 12, whilst permitting the orientation of the cameras 18, 20, 22 relative to the horizontal bar 16 of the T-bar 12 to be adjusted.

Also attached to the horizontal bar 16 of the T-bar 12 by further clamps 30 are a first 32 and second 34 light source. In this embodiment the first light 32 source comprises a light source arranged to irradiate light having a wavelength greater than 570 nm and being arranged to project onto the surface of a patient 8 lying on the mechanical couch 7 of the treatment apparatus 6 a random speckle pattern. An example of a suitable light source would be a slide and slide projector, where the slide bears a non-repeating speckle pattern and the slide projector comprises a filtered light source filtered to prevent light with a wavelength less than 570 nm from being projected onto the slide.

The second light source 34 comprises a conventional light bulb with a filter to allow light with a wavelength of less than 540 nm to pass. The second light source 34 is also arranged to illuminate the portion of a patient 8 which is visible from the cameras 18, 20, 22. The filtration of the light from the second light source 34 prevents the light from the second light source 34, interfering and saturating the speckle pattern generated by the first light source 32.

In use, images of the speckle pattern are obtained by the geometry cameras 18, 22 as these cameras are arranged to detect light having a frequency of greater than 570 nm. These images from the geometry cameras 18, 22 are then subsequently processed so that the position and orientation of the surface of the body of the patient 8 visible from the geometry cameras 18, 22 can be determined and a three dimensional model of the surface of the individual generated as will be described later.

When a textured rendered model of a patient is desired, the images of the patient are obtained from the texture camera 20. These images are then utilised to texture render the model created from the geometry camera 18, 22 images. As the texture camera 20 is arranged only to detect light having a wave length in less than 540 nm, this image does not contain the speckle pattern projected by the first light source 32 but rather corresponds to the visible images perceived by an operator within the treatment room.

FIG. 3 is a schematic block diagram of the computer 5 of FIG. 1. The computer 5 comprises a microprocessor 38 and memory 40. The memory 40 is configured into a number of notional functional modules.

In this embodiment, these functional modules comprise a processing module 42 for controlling the microprocessor 38 to co-ordinate receiving and processing images; a control module 44 arranged to control the microprocessor 38 to receive signals from the keyboard of the computer 5 and co-ordinate the processing by the processing of the other modules; a calibration module 43 enabling microprocessor 38 to calibrate the positioning system so that relative to the point of focus of the treatment apparatus 6 as identified by the laser beam cross hairs 10, the processing module 42 is able to identify the location of the surface of a patient 8; a mechanical couch control module 45 arranged to enable the microprocessor 38 to utilise generated surface models of an individual to generate positioning instructions which are then passed to the mechanical couch 7 of the treatment apparatus 6 so that a patient 8 may be automatically correctly positioned for treatment; an image generation module 46 to enable the microprocessor 38 to generate an image of the portion of the patient being treated and display it on the screen 11 of the computer 5; and a data store 47.

Also provided as part of the computer 5 are a video sync unit 50 and a first and a second frame grabber 51, 52. The first and second frame grabbers 51, 52 are arranged to receive image data from the three cameras attached to each of the camera rigs 1, 2, 3, specifically the first and second frame grabbers 51, 52 are arranged to receive video signals from the geometry cameras 18, 22 of the camera rigs 1, 2, 3 via the video sync 50. Video images for the six geometry cameras (two cameras on each of the three camera rigs) are received by the video sync 50 and passed to the two frame grabbers 51, 52, three to the first frame grabber 51 and three to the second frame grabber 52. The video sync 50 passes timing signals from the first frame grabber 51 to the second frame grabber 52 to ensure that image data from the geometry cameras 18, 22 is acquired simultaneously. By providing two frame grabbers 51, 52, in this way the computer 5 is arranged to receive image data from the geometry cameras 18, 22 of all three rigs 1, 2, 3 simultaneously so that an instantaneous three dimensional model of the surface of a patient 8 can be generated.

Periodically, when requested by the control module 44, the video sync 50 is arranged to obtain image data from the texture cameras 20 of the camera rigs 1,2,3. When a frame of image data from these other cameras is received by the video sync 50 they are passed to the first frame grabber 51, and then onto the processing module 42. These images which comprise images generated from light having a wavelength less than 540 nm are then subsequently used to texture render the three dimensional model generated by the image generation module 46. In contrast to the geometry camera images received simultaneously for a particular frame, the texture camera images represent an images from the subsequent frame separated by approximately 40 milliseconds from the geometry camera images, utilised to generate a three dimensional model. However, as the appearance of the surface of an individual 8 varies very little over this time period, this mismatch in timing does not appreciably diminish the performance of the system. In contrast, simultaneous geometry camera images from all the geometry cameras are required to enable a highly accurate model of the surface of a patient 8 to be calculated.

Figure 4:
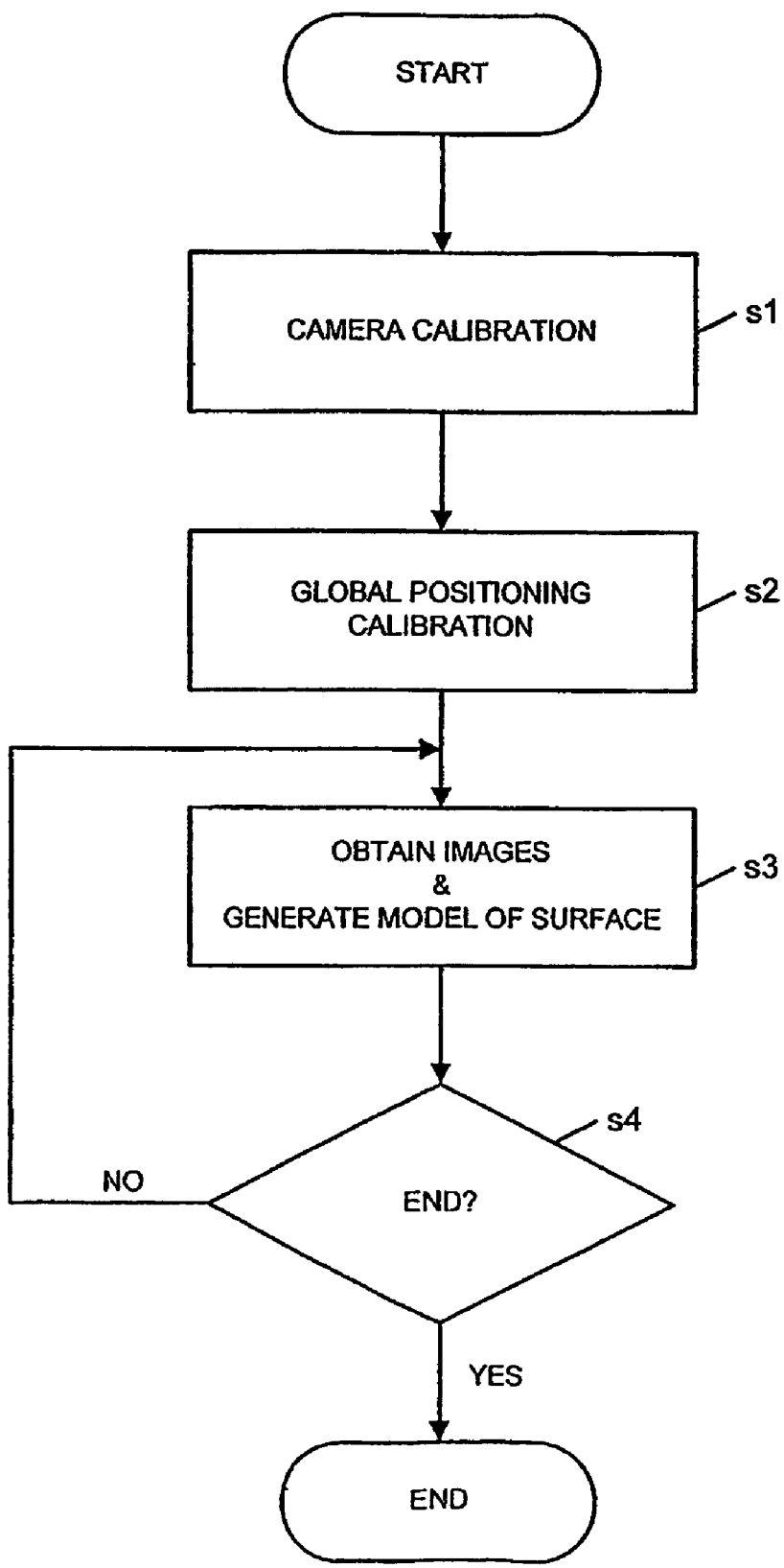
FIG. 4 is a an overview flow diagram of the processing of the computer of FIG. 3.

The overall processing of the computer 5 will now be described in detail. FIG. 4 is a flow diagram of the processing of the computer 5 in accordance with this embodiment of the present invention. Initially a user via the keyboard of the computer 5 identifies to the control module 44 that the computer 5 is to process the images received from the three camera rigs 1, 2, 3 to generate a set of calibration parameters to identify the relative positioning of the cameras 18, 20, 22 on each of the rigs 1, 2, 3. When such an instruction is received from the keyboard the calibration module 43 is invoked and camera calibration (S1) is then performed.

A calibration sheet comprising a 40×40 cm sheet of flat rigid material such as aluminium or steel on which a pattern revealing a 20×20 matrix of circles at known positions on the surface of the sheet is provided. Additionally, towards the centre of the calibration sheet are four smaller markers adjacent to four circles the centres of which together identify the four corners of a square of known size. When calibration is to occur, the sheet is held in position on the mechanical couch 7. Images of the calibration sheet are then obtained by all of the cameras 18, 20, 22 of a camera rig 1, 2, 3 being calibrated. These images are then processed by the calibration module 43 by initially performing a thresholding operation on the obtained images. The thresholded images are then processed to identify within the image the positions of the four markers in the images and their associated circles. This can be done either automatically using conventional techniques or alternatively, a user may identify the four circles manually.

From the relative positions of circles identified by the markers in the images, a projective transformation is determined which accounts for the estimated centres of the identified circles defining the corners of a parallelogram in the image which arises due to the relative orientation of the calibration sheet and the camera obtaining the image. In this embodiment the transformation determined is an estimated transformation for distorting the image so that the circle centres correspond to the corners of a perfect square.

The calculated transform is then applied to each of the identified circles in turn to transform the oval shapes of the circles. A more accurate estimate of the positions of the centres of the four circles is then determined by identifying the centre of the transformed circles and utilising an inverse transform to determine the corresponding position of the estimated circle centre in the original image. These updated estimates are then revised to determine a new transformation. By repeating the process a number of times an accurate estimate of the transform required to account for the relative orientation of the calibration sheet can be made.

Using the determined transform, the expected positions of all of the circles on the sheet appearing in the image are then calculated, the portions of the images in the vicinity of each of the estimated circle centres are then processed individually. Firstly, from the thresholded image, the portion of an image corresponding to a circle on the calibration sheet is identified. The identified area is then subjected to the calculated transform so as to transform the elliptical appearance of the circle in an image due to the relative orientation of the calibration sheet to the camera being calibrated. The actual centre of the transformed circle is then determined in a similar manner as has previously been described and then the projection of that actual centre appearing in the image is then calculated by applying the inverse of the calculated transform to the co-ordinates of the newly estimated circle centre.

When the co-ordinates for all the centres of each of the representations of the circles on the calibration sheet have been calculated for an image, the relative orientation of the different cameras 18, 20, 22 on one of the camera rigs 1, 2, 3 can then be calculated from the relative positions of these points in the images and the known relative locations of these circles on the surface of the calibration sheet as is described in detail in "A Versatile Camera Calibration Technique for High-Accuracy 3D Machine Vision Metrology Using Off the Shelf TV Cameras and Lenses", Roger Tsai, IEEE Journal of Robotics and Automation, Vol. Ra-3, No. 4, August 1987. Further from the relative positions of the points in the individual images internal camera parameters such as the focal length, and radial distortion within the camera images can also be determined. This information is then stored within the data store 47 of the memory 40 of the computer 5 for use in subsequent generation of accurate three dimensional representations of the surface of a patient.

When the camera positions and internal camera parameters have been determined for all of the cameras 18, 20, 22 for all three of the camera rigs 1, 2, 3, the positioning of the cameras relative to the focussing point of the treatment apparatus 6 is then determined (S2).

In this embodiment as has previously been described a laser projection system 9 is provided which is arranged to project three cross hairs 10 identifying the focussing point of the treatment apparatus 6. This focussing point is also known as the isocentre for the treatment apparatus 6. In a conventional manner the calibration of this laser equipment and the treatment apparatus 6 is performed so that a user is able to use the projection of the laser cross hairs 10 being planes of light which intersect at the isocentre to identify the isocentre of the treatment apparatus 6 when treatment is occurring. The laser cross hairs 10 are then utilised to enable the relative positions of the cameras of the camera rigs 1, 2, 3 to be determined relative to the isocentre.

Figure 5A:
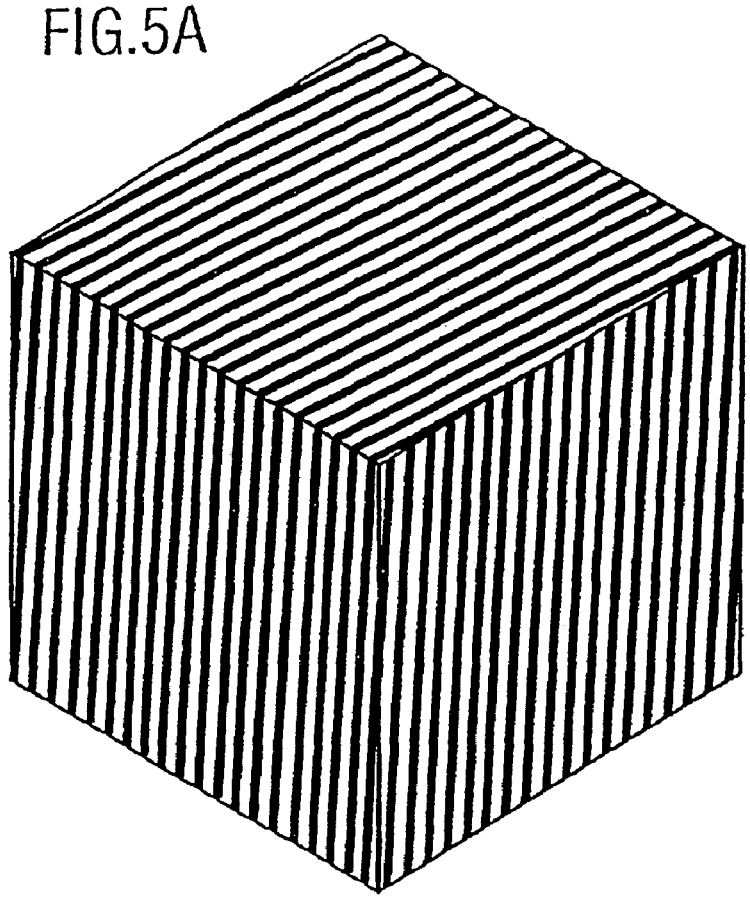
FIG. 5A is an illustration of a calibration device utilised to calibrate the positioning system of FIG. 1.

Specifically as is illustrated in FIG. 5A, a calibration cube comprising a cube of known size on whose surfaces are a series of thin black and white stripes is placed on the mechanical couch 7 in the vicinity of the focussing point of the treatment apparatus 6. As can be seen from FIG. 5A the stripes on the calibration cube are oblique relative to the sides of the cube. The illumination within the treatment room is then switched off so that the cube is only illuminated by the cross hairs generated by the laser projection apparatus 9. Images of the cube illuminated in this manner are then obtained by the cameras 18, 20, 22 in each of the camera rigs 1, 2, 3.

Figure 5B:
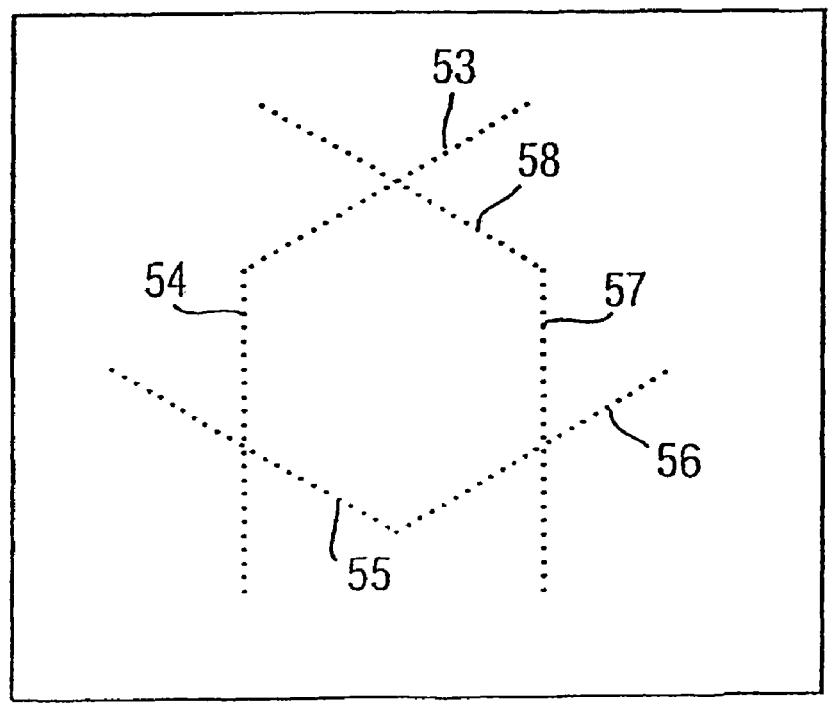
FIG. 5B is an exemplary illustration of an image obtained utilising the calibration device of FIG. 5A.

FIG. 5B is an exemplary illustration of an image obtained by one of the cameras of the calibration cube illuminated only by the cross hairs generated by the laser projection apparatus 9. As can been seen in FIG. 5B the image comprises a number of discrete points corresponding to portions of the cross hairs which are reflected by the white stripes on the calibration cube.

Processing pairs of images obtained by the geometry cameras 18, 22 from a camera rig 1, 2, 3 and the known relative orientation and internal parameters of the cameras 18, 22 on each rig, enables three dimensional co-ordinates of the points appearing in the images relative to the camera rigs 1, 2, 3 to be determined.

As these points correspond to points lying on planes intersecting with the surface of the calibration cube, groups of the points identify planes in space. The relative positioning of the cameras 18, 22, 24 and the focussing point of the treatment apparatus 6 can then be identified by determining the point of intersection of three planes which are identified by groups of points corresponding to pairs of the identified lines 53, 54; 55, 56; 57, 58 as this will be the only point in the treatment room where all the cross hairs intersect. Data identifying the co-ordinates of the isocentre relative to each of the camera rigs 1, 2, 3 is then stored in the data store 47 of memory 40 of the computer 5 so that the relative positioning of the cameras 18, 20, 22 of the three camera rigs 1, 2, 3 relative to this isocentre can be utilised as a fixed point to identify the relative position of a patient 8 on the mechanical couch 7.

After the positions of all the cameras 18, 20, 22 of the camera rigs 1, 2, 3 have been determined relative to the focussing point of the treatment apparatus 6, the cameras 18, 20, 22 can then be utilised to generate representations of the surface of a patient 8 lying on the mechanical couch 7. In order to do so an instruction is entered via the keyboard of the computer 5. When this is detected by the control module 44, the control module 44 then causes the processing module 42 to start processing images received from the video cameras to generate a three dimensional model of the surface (S3) received in those images. This processing continues until an instruction to stop (S4) generating images is received from the keyboard of the computer 5 at which processing of images and generation of surface models ends.

The processing of the processing module 42 for generating models of the surface of a patient 8 on the mechanical couch 7 of the treatment apparatus 6 will now be described in detail.

Figure 6:
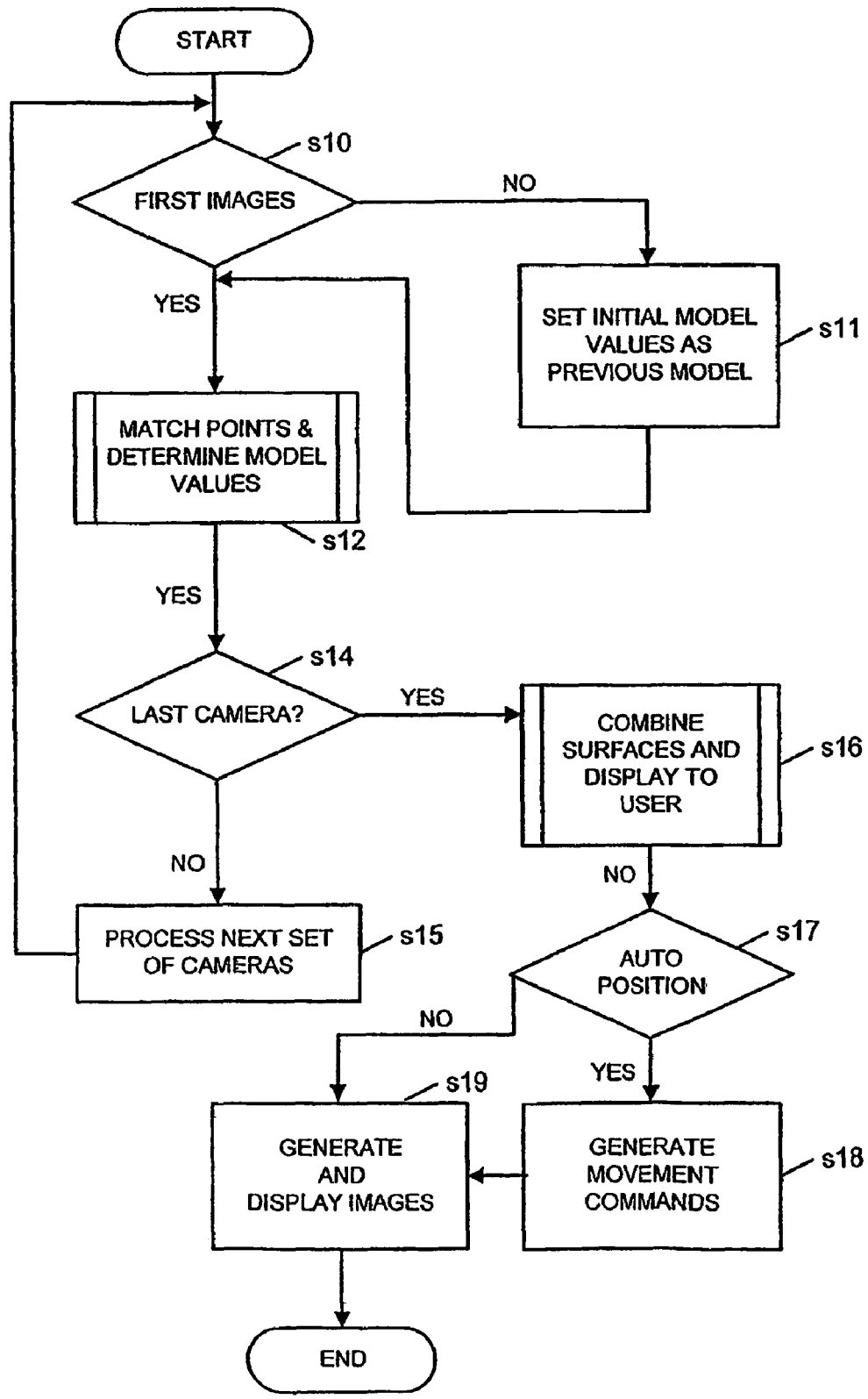
FIG. 6 is a flow diagram of the processing of the computer of FIG. 3 for generating models of individuals from received images.

FIG. 6 is a flow diagram of the processing by the computer 5 when a set of images are received by the processing module 42 from the frame grabbers 51, 52. Initially (S10) the processing module 42 determines whether the images received are the first of a set of images of the patient 8 which a model is being generated. If this is not the case, the processing module 41 will already have stored within the data store 47 data identifying the affine transformations required to match points in images obtained by one of the geometry cameras 18 of a camera rig in the corresponding image obtained by the second geometry camera 22 in the same camera rigs. If this is the case, the processing module 42 utilises (S11) the previously stored data in the data store 47 to initialise the model data being generated for the current images. The processing module 42 then (S12) proceeds to match points appearing in images obtained by the geometry cameras 18, 22 for the first of the camera rigs 1, 2 3 as will now be described in detail with reference to FIGS. 7A and 7B and 8.

Figure 7A:
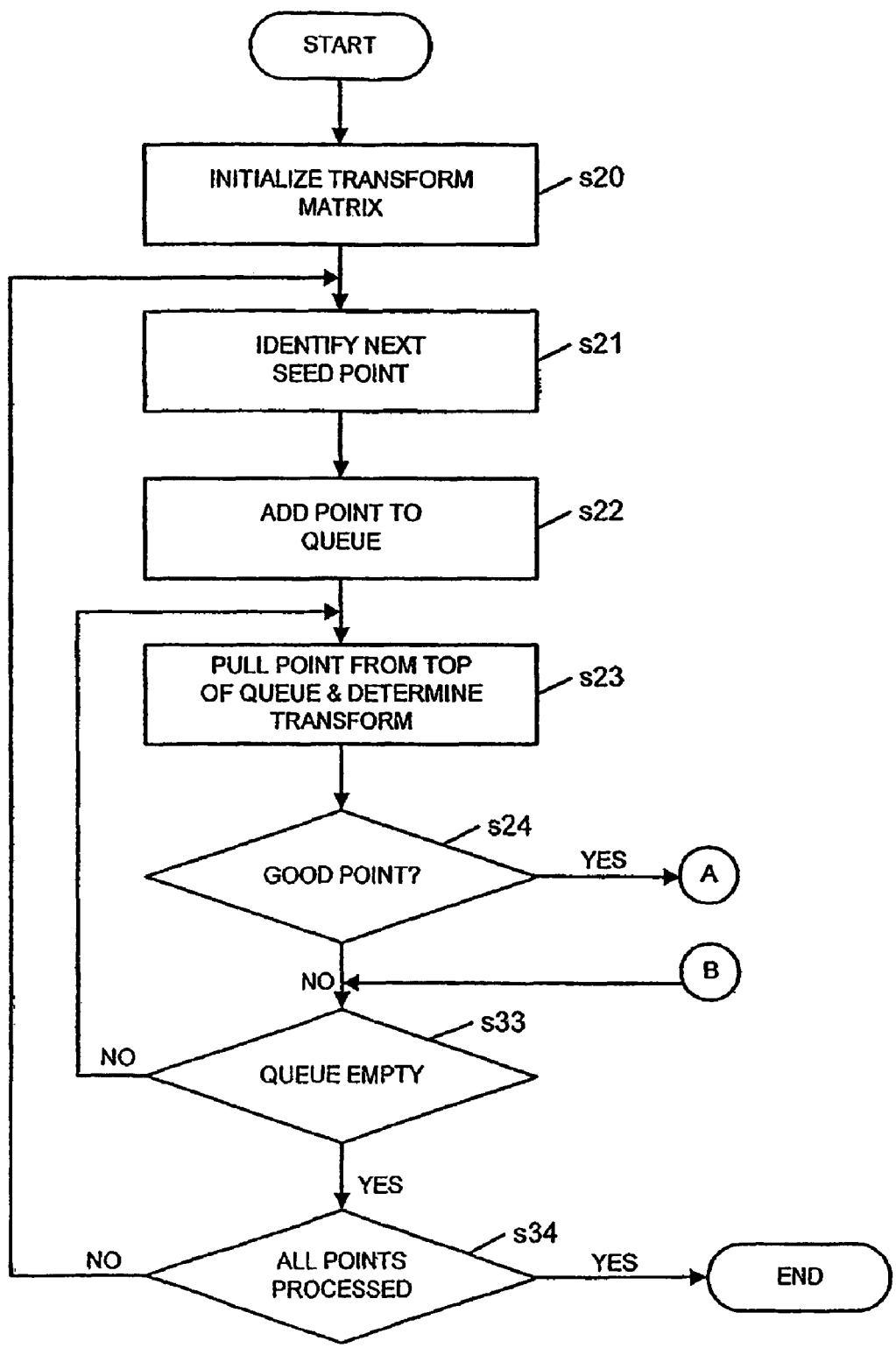
FIGS. 7A and 7B are a flow diagram of the processing of the computer of FIG. 3 for matching points in received images to determine the orientation of points on the surface of an individual.
Figure 7B:
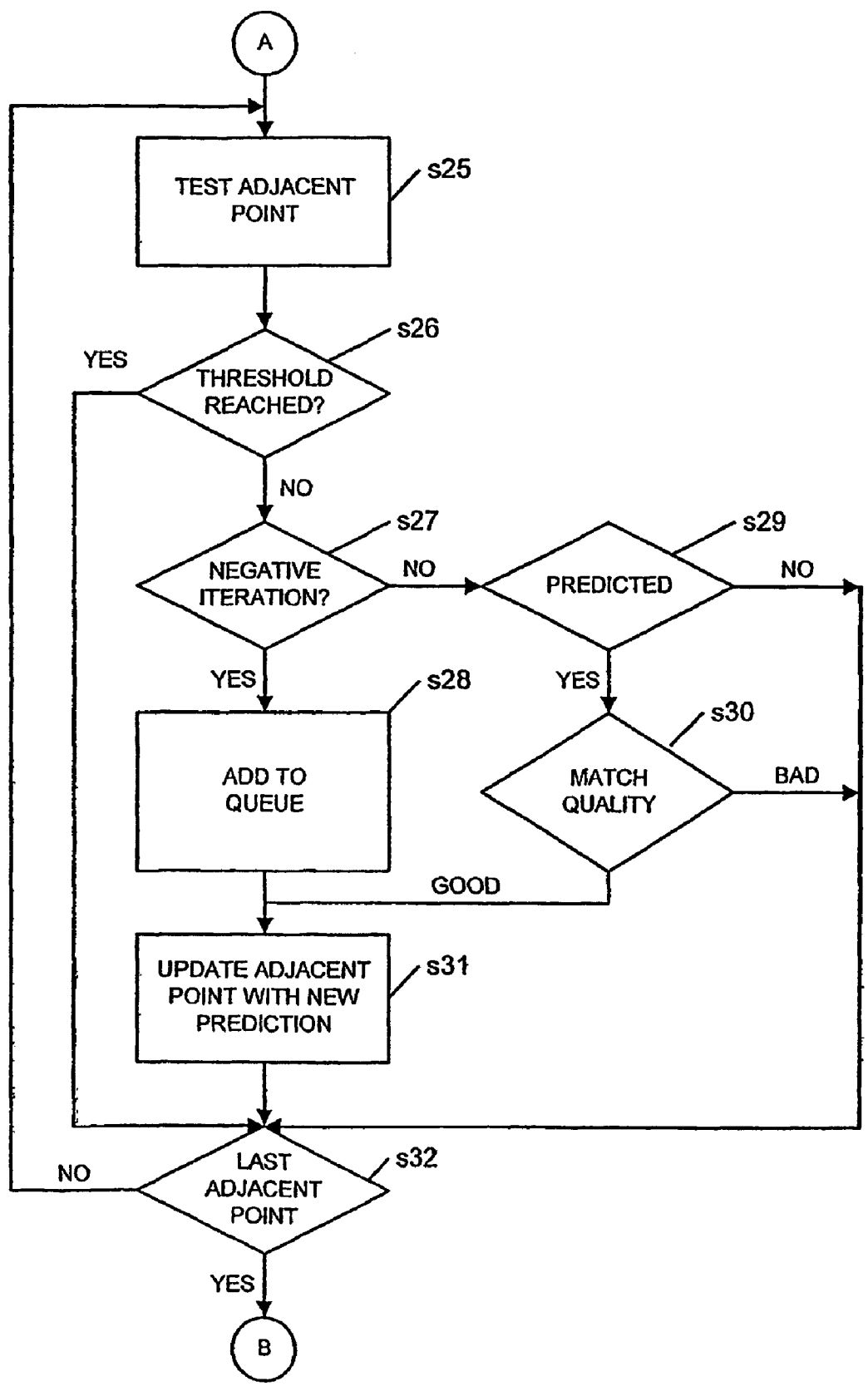

FIGS. 7A and B are a flow diagram of the processing of images by the processing module.

As a first step in processing pairs of images received from the geometry cameras 18, 22 the processing module 42 initialises (S20) the matrix of match parameters identifying the manner in which points in an image obtained from one of the geometry cameras 18 are matched in points in the image received from the other geometry camera 22.

Figure 8:
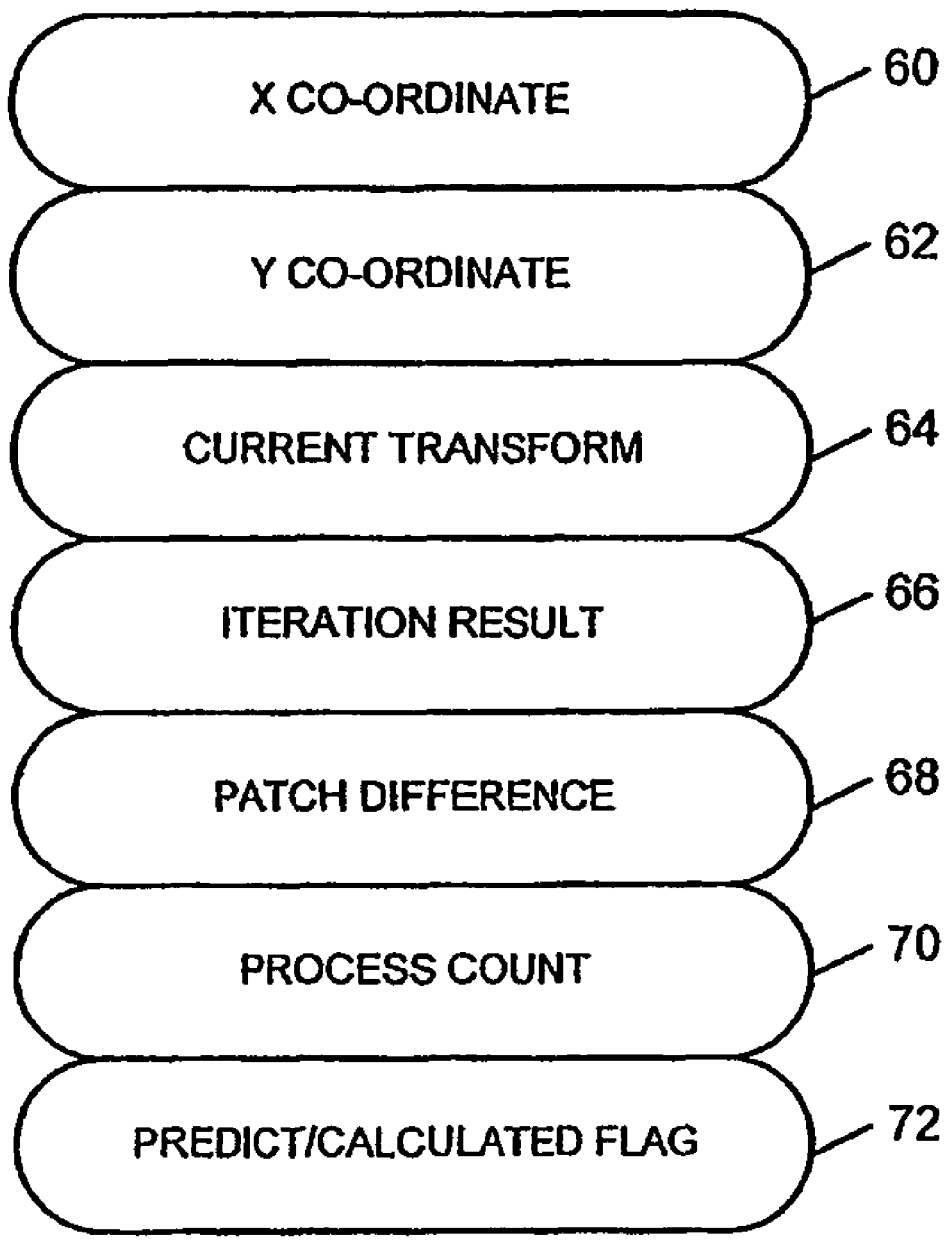
FIG. 8 is a schematic illustration of a data structure for storing data utilised to perform the processing of FIGS. 7A and 7B.

FIG. 8 is a schematic illustration of a data structure for storing data utilised to match points in the images of one geometry camera 18 of a camera rig 1,2,3, to a corresponding point in images received from the other geometry camera 22 of the camera rigs 1, 2, 3. The data structure of FIG. 8 is stored in the data store 47 for each of a matrix of points in the image of the first geometry camera 18 so that corresponding points in a corresponding image received from the other geometry camera 22 from the same camera rig can be identified.

For each of the points in the image which identify a matrix of points in the image the following data is stored: an x coordinate 60 and a y coordinate 62 identifying the location of a current transform 64 identifying the manner in which a patch centred on the identified point in the first image is to be distorted so as to match the corresponding portion of a matching patch in a second image; an iteration result 66 identifying the number of iterations utilised to calculate the current transform 64 or a negative code number identifying a lack of convergence; a patch difference 68 identifying the total difference in grey scale values between the patch identified by the x and y coordinates 60,62 and the corresponding patch in the other geometry image; a process count 70 identifying the number of times the point identified by the x coordinate y coordinate data 60,62 has been processed and a predict/calculated flag 72.

When the matrix of match parameters for a pair of images is first generated for all of the pairs of x coordinates and y coordinates 60,62 the current transform 64 iteration result 66, patch difference 68, process count 70, and predict/calculated flag 72 are set as follows:

| | |
|---|---|
| Current Transform = | identity |
| Iteration Result = | −99 |
| Patch Difference = | 1000 |
| Process Count = | 0 |
| Predict/Calculated Flag = | predicted |

If, however, a pair of geometry images from the camera rig 1,2,3 has already been processed, in this embodiment instead of initially setting the current transform to being the identity transform, the previously calculated transform for that point is utilised when initialising the matrix of match parameters for the next pair of images from that camera rig to be processed. In this way, the processing module 42 is arranged to assume that as an initial estimate of the surface of the patient, the shape of the patient 8 being monitored does not vary. As this is normally a reasonable first approximation, this ensures that the initial transformation selected as a starting point is to close to being correct, and hence the speed of which images can be processed is increased.

The processing module 42 then (S21) identifies the next point in an image received from a geometry camera 18 which is to be matched to a corresponding point in a corresponding image from the other geometry camera 22 from the same camera rig 1, 2, 3. This is achieved using a conventional search, in 3D space.

Specifically, the image processing module, 42 first identifies the next point in the image which has not been processed. This is achieved by scanning the matrix of match parameters to find an unmatched point. Using the co-ordinates of the selected point and the relative orientations of the texture cameras 18, 22 on a camera rig, the image processing module then selects potential matches for the point in one texture image as corresponding to the point from the other image by calculating expected positions for the point assuming the point is a various depths away from the cameras. When a potential match for the next point has been identified, data identifying the coordinates of this point and a potential match are added to the bottom of the queue (S22) of points to be processed.

The image processing module 42 then (S23) selects the point at the head of the queue for processing and determines a transformation required to match a patch centred on the point being processed with a corresponding patch centred on the co-ordinates for the identified potential match for the point.

Assuming that the images, image 1 and image 2 being processed are represented by functions f and g such that Image 1=$f(x,y)$ Image 2=$g(x,y)$ In a region being matched there will exist a transform T such that $f(x_i,y_i)=g(T(x_i,y_i))$, where $x_i,y_i$ are patches in region being matched.

As a starting point, the transforms necessary to match the point in the first image to the identified potential match centre used together with the stored transform 64 for the current point to account for an affine distortion of the patch area can be used to match the two patches.

Assuming that the transform T represents an affine transformation, which is a reasonable approximation, the transformation T(x,y) can be represented as:

$T(x,y)=(ax+by+c,dx+ey+f)$

Therefore in the regions which correspond to one another $f(x_i,y_i)=g(ax_i+by_i+c,dx_i+ey_i+f)+\epsilon$ where $\epsilon$; is an error term which reflects noise between the images.

Values for a,b,c,d,e and f can then be determined iteratively from the initial starting transformation for matching the patches by relacing these values by $a+\delta a$, $b+\delta b$, $c+\delta c, d+\delta d$, $e+\delta d, e+\delta e, f+\delta f$ and approximating the resulting non linear function by a linear expression that can be solved using a least squares matrix technique.

Thus, if $g_x(x_i',y_i')$ and $g_y(x_i',y_i')$ are the derivatives of function g in the x and y directions evaluated at the point $(x_i,y_i)$ then from the above $$f(x_i,y_i)-g(x_i',y_i')=(xg_x^i\delta a+yg_x^i\delta b+g_x^i\delta c+xg_y^i\delta d+yg_y^i\delta e+g_y^i\delta f)+\epsilon$$

with $(x_i',y_i')=(ax_i+by_i+c,dx+ey_i+f)$ and $$g_x(x_i',y_i')=g_x^i, g_y(x_i',y_i')=g_y^i$$

and hence in matrix form $$f(x_i,y_i)-g(x_i',y_i')=(xg_x^i,yg_x^i,g_x^i,xg_y^i,yg_y^i,g_y^i)*(\delta a,\delta b,\delta c,\delta d,\delta e,\delta f)^T+\epsilon$$

From the above the difference between the two patches $f(x_i,y_i)$ and $g(x_i',y_i)$ is equal to the matrix multiplication of the two matrices on the right hand side plus the error $\epsilon_i$; and hence B=A$\delta$D+E where B is the difference between the two regions whose ith entry is $f(x_i,y_i)-g(x_i',y_i')$, D=(a,b,c,d,e,f), $\delta D=(\delta a, \delta b, \delta c, \delta e, \delta f)$ and A is a matrix whose ith row is $(xg_x^i,yg_x^i,g_x^i,xg_y^i,yg_y^i,g_y^i)$ which is dependent upon image derivatives and E is an error vector whose ith entry is $e_i$.

Assuming $\xi(E)=0$ and $\xi(EE^T)=\sigma^2 P^{-1}$ where $\xi$ is the expectation operator and $\sigma$ is a numerical factor and P is a matrix B=A $\delta$D+E forms a Gauss-Markov estimation model, which can be solved by pre-multiplying by $A^T P$ so that $A^T PB=A^T PA\delta D+A^T PE$. Dropping the error term these can be solved by Cholesky Decomposition giving an unbiased, minimum variance estimator of $\delta D$.

An iterative determination of the values for a,b,c,d,e and f can therefore be made staring from the initial transformation and calculated differences and derivatives for the two patches. With each iteration A should be updated to account for the new calculated transform T for the new values of a,b,c,d,e, f. This can however be more rapidly achieved by estimating the updated values for A for the next iteration from the previous values for A,B and D above as follows.

From the above for points within portions of the images f(x,y) and g(x,y) being matched $B=A\delta D+E$ where $\delta D=(\delta A,\delta b,\delta c,\delta d,\delta e,\delta f)^T$ and A is a matrix whose ith entry is $(xg_x^i, yg_x^i, g_x^i, xg_y^i, yg_y^i, g_y^i)$.

Noting that A is equal to the derivative of g with respect to the parameters (a,b,c,d,e,f), if after j iterations and $B_j,g_j,D_j A_j$ are estimated values for B,g,D and A and assuming the patch in the first image f(x,y) stays fixed then after one iteration it is possible to determine $$\delta D = D_1 - D_0 \text{ and}$$

$$\delta g = g_1 - g_0$$
$$= (f_1 - g_1) - (f_0 - g_0)$$
$$= B_1 - B_0$$

which gives information about the derivative of g in the direction $\delta D$. Noting that, if $A \delta D=\delta g$, the derivative of g will satisfy the information obtained, it follows that an update of the iterative solution of A will be a reasonable solution where the above holds true. This can automatically be achieved by using the update.

$$A_j = A_{j-1} + (\delta g_j - A_{j-1} \delta D_j)(\delta D_j^T)/(\delta D_j^T \delta D_j)$$

where $\delta D_j = D_j - D_{j-1}$ and $\delta g_j = B_{j-1} - B_j$;
and hence by calculating for patches being matched an initial difference matrix $B_0$ and an initial derivative matrix $A_0$ using the initial estimated transform from an iterative solution for the actual transform T can be calculated solely by recalculating the difference matrix $B_j$ for each iteration and updating the transform T and the derivative matrix using this recalculated difference matrix $B_j$ in the manner described with this update being a reasonable approximation.

In this embodiment, the upper limit for the number of iterations is set to 10 and a patch is identified as having converged if the updated transform varies the x, y co-ordinates being matched by less than 0.03 pixels. In addition to checking whether convergence has been achieved, at each iteration in this embodiment a check is also made as to whether the calculated transform has failed either by introducing excessive expansion of an area, or varying the x, y co-ordinate of a potential match by 2 or more pixels or where a transform results in searching for a match outside the image area. If any of these conditions are met, this indicates that no realistic match will be reached.

Additionally, after it has been determined that convergence has been achieved, the calculated transform for a point is tested to determine the extent of uncertainty of the match.

More specifically a value indicative of the standard deviation of matched points in a pair of matched patches can be determined and a potential match rejected if the standard deviation is excessive.

In this embodiment, this is achieved by initially determining a variance factor for the potential match of patches by calculating the residual vector V indicative of the difference between $A\delta D$ and B. The variance factor is then equal to $$\frac{V^T P V}{r}$$

where r is the number of rows in A less the number of columns in A (ie the number of observances (pixels) in the patches less the number of degrees of freedom for matching patches).

Strictly the standard deviation for the different parameters in the match could then be calculated using the variance factor and a calculated matrix $(A^T P A)^{-1}$. However, in this embodiment rather than calculating the entire matrix, since the Cholesky decomposition of $A^T P A$ is calculated at each interation, this decomposition is used to calculate a number of selected entries of $(A^T P A)^{-1}$ from which an uncertainty measure can be calculated.

Since by definition for any matrix M the inverse matrix $M^{-1}$ is such that $MM^{-1}=I$ entries in $(A^T P A)^{-1}$ can be calculated by solving the equation $$(A^T P A)X = n$$

where n is a single column vector with a single non zero entry set equal to one.

In this embodiment, the first three entries in the first three columns which are indicative of the uncertainty of the x co-ordinate are calculated and the second three entries in the second three columns which are indicative of the uncertainty of the y co-ordinate are calculated.

These two 3 by 3 matrices are then processed to calculate for a point having co-ordinates x,y, two uncertainty measures, one using each matrix where $$\text{uncertainty measure} = \text{variance factor} \begin{pmatrix} x^2 M_{0,0} + y^2 M_{1,1} + M_{2,2} + \\ 2xy M_{0,1} + 2y M_{1,2} + 2x M_{0,2} \end{pmatrix}$$

and $M_{ij}$ is the ith entry in column j from the respective 3 by 3 matrices.

A match for a point is then rejected if either the uncertainty measure for the x co-ordinate or the y co-ordinate exceeds a threshold which in the embodiment is set equal to 0.1.

In this way at each iteration a potential match is rejected if the calculated transform for a match is determined to be unrealistic. Finally all potential matches which may be realistic are subjected to a second check and any borderline matches are rejected if the uncertainty of a match is found to be too great.

When convergence is reached data identifying the number of iterations used to reach a result is stored. Alternatively if the transform fails or the uncertainty of a match is too great, a negative number identifying that an error has occurred is stored for the point as an iteration result.

Thus when a point is processed (S23) an iterative determination of the transform of a patch centred on the point necessary to match the patch with a corresponding patch in the image received from the other geometry camera 22 of the same camera rig 1,2 3 is made. Data for that point is then stored in the data store 47 where the iterative transform is stored as the current transform 64 the number of iterations utilised to determine the result or a negative error number is stored as the iteration result 66 a patch difference value being the absolute grey scale difference for the patch transformed in the manner identified by the current transform 64 compared with the corresponding patch in the image received from the other geometry camera 22 the process count 70 is incremented by one and the predicted/calculated flag 72 is set to calculated.

The processing module 42 then (S24) determines whether the match made for the point being processed is a good match. In this embodiment this is achieved by utilising the iteration result data 66 of the patch. If, for any reason the number of iterations required to determine the transform 64 for matching the patch from one invention to the corresponding patch in the second image is too high or negative this indicates that it was not possible to determine a match for the point. If, however, this is not the case the processing module 42 utilises the transform 64 for the current point to act as seed data for initiating matches for adjacent points as will now be described in detail with reference to FIG. 7B.

Initially (S25) the processing module selects one of the four adjacent points adjacent to the point corresponding to the patch which has just been processed. That is to say the points at which the x coordinates and y coordinates 60, 62 stored in the data store 47 are one greater and one less than the patch which the x coordinates and y coordinates 62, 62 for the patch which has just been processed.

When the adjacent point has been selected the processing module 42 then (S26) determines whether the process count 70 for that point is less than three. If this is the case this indicates that the adjacent point which has been selected has not previously been processed more than three times. If the point has been processed three times, this indicates that there have been difficulties in generating a satisfactory match for the point. In order to speed the processing of images, in this embodiment under these circumstances the point is not considered for any further attempts at matching the point. In other embodiments the process count could be required to be a different value with the result more or fewer attempts at identifying a match for a point occur.

If the process count for a point is less than three, the processing module 42 then determines (S27) whether the selected point is associated with a negative iteration result 66. This could arise either because the point has never been processed before or because the processing module 42 failed to determine a match for the patch last time the patch was processed. If the iteration result 66 is negative, the processing module 42 sets the predicted/calculated flag 72 for the point being considered to be predicted and adds (S28) the point to the bottom of the queue.

Thus in this way, the processing module 42 causes a queue of points to be identified which enable portions of the images received from the geometry cameras to be matched in a manner in which adjacent portions of an image are processed consecutively. The adding of points to queue in this manner also enables an ordering of points to be made which requires minimal processing power and as will be described in detail later, enables the best matches for adjacent points to be used as seed values for subsequent processing.

If the processing module 42 determines (S27) that the iteration result for a point is not negative, the processing module 42 then determines (S29) whether the adjacent point being tested has a predict/calculated flag set to predicted. If the predicted/calculated flag is set to calculated, this indicates that a transform for the point in question has already successfully been determined. However, if the predicated/calculated flag 72 is set to predicted, this indicates that the transform for the point identified by the current transform data 64 is only an initial estimate of a starting point for the transform necessary to match a patch centred on the identified x coordinate and y coordinate 62 of the selected adjacent point or when the point was processed previously, the processing module 42 failed to determine a satisfactory match for the point.

If the predict/calculated flag 72 is set to predicted the processing module 42 then (S30) compares the patch difference data 68 for the selected adjacent point with the calculated patch difference applying the current transform 64 of the previously processed point to a patch centred on the identified by the adjacent point being tested. If the application of the transform for the previous point which has been processed results in a better match between patches in the geometry images, this is indicated by the stored patch difference 68 for this adjacent point being greater than the calculated patch difference determined by applying the transform calculated for the previously processed point to the patch centred on the adjacent point being considered. If this is the case or alternatively automatically after adding a point associated with a negative iteration value to the queue of points to be processed (S28) the processing module 42 (S31) updates the patch difference data 68 and the current transform 64 for the adjacent point being considered by setting the current transform 64 for the adjacent point equal to the transform for the previously processed point and the patch difference 68 for the adjacent point to the calculated patch difference calculated utilising the transform for the previous point.

After either the processing module has determined (S29) that the calculated flag 72 of the point is set to calculated, or the processing module 42 has determined (S30) that the transform for the previously processed point is not an improvement on the match for the current transform 64 for the adjacent point being considered or (S31) the data for the adjacent point has been updated, the processing module 42 then (S32) determines whether all of the points adjacent to the point which has just been processed have been considered and updated if necessary. If this is not the case the next adjacent point is then considered (S25-S31). Thus in this way all of the four points adjacent to a point which is processed are considered one after another and the current transform data 64 for those adjacent points which have not already had satisfactory transforms calculated for them are updated to correspond to better initial estimates of transforms for those points.

Returning to FIG. 7A after current transform data 64 for adjacent points has been updated the processing module 42 then (S33) determines whether the queue of points to be processed is empty. If this is not the case the next point in the queue is selected (S23) and a transform for that next point is calculated and estimates of transforms for the adjacent points are updated where required (S24-S32).

If the queue of points is empty the processing module 42 then determines whether all of the points in the image responding to patches have been processed (S34) if this is not the case a new seed point (S21) is identified and further points are processed (S22-S33). When all of the points in the image have been processed (S34) the processing of the processing module comes to an end.

As an initial first approximation, it is reasonable to assume that adjacent parts of a patients body 8 are flat and orientated in the same direction relative to the cameras of the camera rigs 1, 2, 3. By processing patches in the images received from the geometry cameras 18, 22 in the way described above, when the orientation of one point within the image has been determined, this orientation is utilised in selecting an initial start point for calculating the orientation of adjacent points. As the best orientation of either an identity transform, the orientation for a point determined from a previous pair of images, or the orientation of adjacent processed points is used as a start point for determining the transform, the intensive processing necessary for the iterative accurate determination of the orientation of points is minimised. The speed at which the processing module 42 is able to determine the orientation of the points appearing in the entire image is thereby increased.

Further, by adding a point to the queue of points for processing when, an adjacent point is processed and the iteration result 66 for the point being considered indicates that no satisfactory match has been determined, the processing module 42 ensures that all available seed data is utilised to attempt to find a match for each point. Specifically, if an initial attempt at a match fails, a point is tested again by using any subsequent seed data determined for any adjacent points. Further although no attempt is made to identify the highest quality matches and process those matches first, the present embodiment ensures that by the time a point is processed all available information for any adjacent points is taken into account when selecting an initial stating transform. The adding of points to a queue of points to be processed also ensures that adjacent areas are processed together.

In this embodiment points in pairs of images are matched by comparing the content of a patch centred on a point in one image with the result of transforming a patch centred on a point in the other image. The matching of points based on the matching of patches in this way ensures that the errors arising from attempting to match patches viewed from different angles are minimised. In particular, by processing patches centred on a point as opposed to patches identified by the co-ordinates of a corner of the patch the matching achieved between points in the three different camera rigs 1,2,3 is largely consistent.

Returning to FIG. 6 when all the points in a pair of images received from the two geometry cameras 18, 22 of the camera rig 1, 2, 3 have been processed, the processing module 47 then (S14) determines whether images for all three camera rigs 1, 2, 3 have been matched. If this is not the case the processing module 47 then selects the next set of geometry cameras 18, 22 (S15) and proceeds (S10-S14) to determine transformations to match portions of images received by the geometry cameras 18, 22 of that camera rig 1, 2, 3.

When transformations have been determined for all three pairs of geometry images for a frame the processing module 42 then (S16) proceeds to generate a three dimensional wire mesh model of the surface of a patient 8 utilising the calculated matches.

Figure 9:
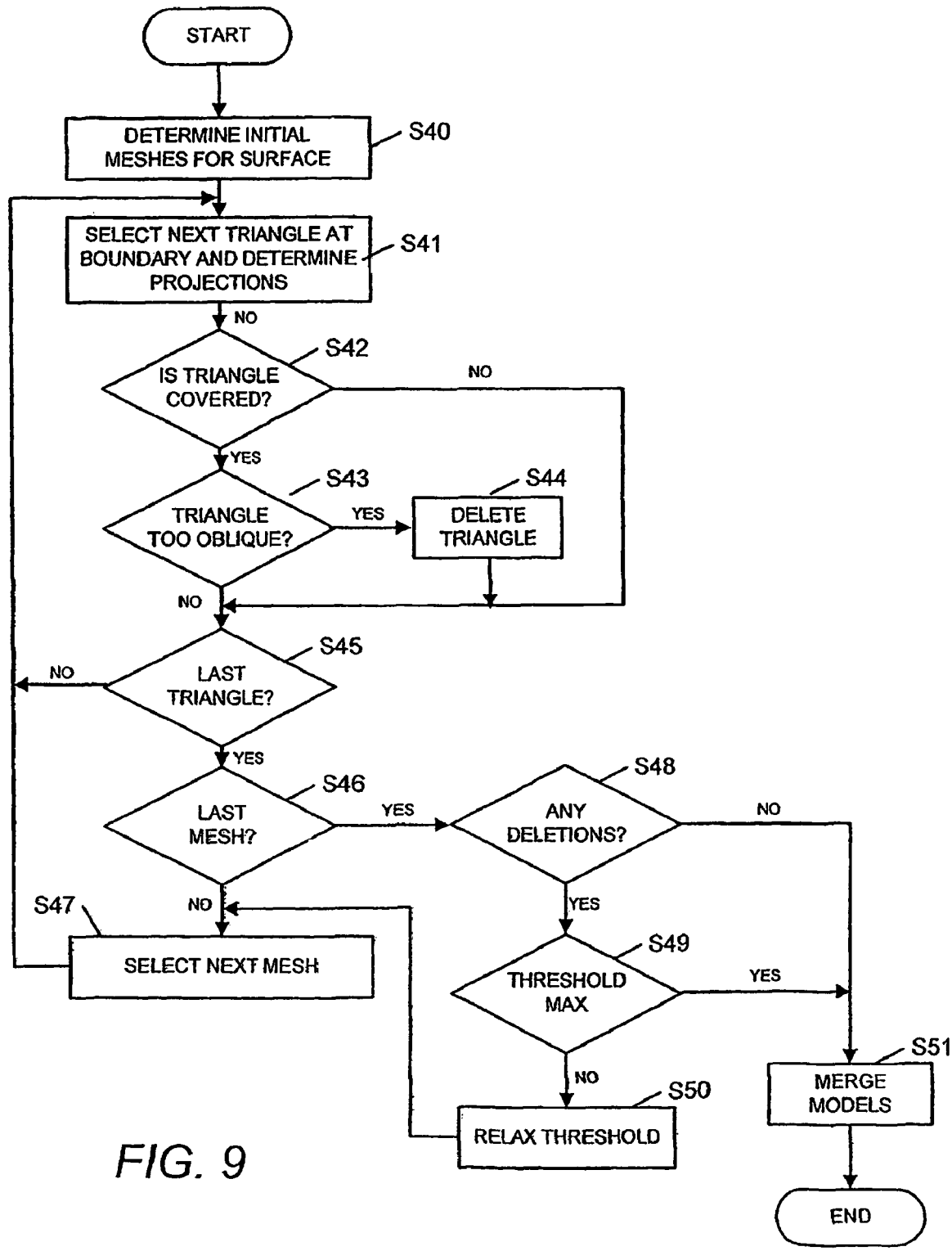
FIG. 9 is a flow diagram of the processing of the computer of FIG. 3 to generate a model of the surface of an individual.

Specifically as is shown in detail of the flow diagram of FIG. 9, the processing module initially (S40) utilises the current transform data 64 associated with points identified by the x coordinates 60 and the y coordinates 62 of data stored within the data store 47 for each pair of images together with the stored data identifying the relative orientations of the geometry cameras 18, 22 of the camera rigs 1, 2, 3 and intrinsic properties of those cameras 18,22 to generate three three dimensional wire mesh models of the surface of a patient 8 as visible from the three camera rigs 1, 2, 3. In this embodiment the calculation of the wire mesh models of the surfaces as viewed from the three camera rigs 1, 2, 3 utilising this data is entirely conventional.

The processing model 42 then selects a first model for processing. The processing module (S41) then identifies a triangle from the selected model defined by points at the edge of the selected wire mesh model. The processing module then determines for the selected triangle the projection of the selected triangle into the image planes of the geometry cameras utilised to generate the other two models. The processing module then (S42) determines whether the selected triangle covered by a portion of the models generated from the other two camera rigs.

Specifically the processing module determines for each of the projections of the vertices of the selected triangle into the view points of the other camera rigs, whether projections are also represented by the model generated using image data from the camera rig represented by that image plane. If this is the case for all three of the projected vertices into a particular image plane, the processing module 42 then determines whether the triangles from the model generated utilising that image plane correspond to triangles in space which are relatively close to the triangle in space represented by the model being processed. This will be the case where the projected triangle is in fact representative of the same portion of the surfaces of a patient as part of the model generated utilising that particular image plane.

If this is the case, the processing module 42 then (S43) determines whether the triangle being processed should be deleted. In this embodiment, a twofold test is utilised to determine whether a particular triangle should be deleted. The processing module 42 initially determines the relative orientation of the triangle being processed relative to the image plane utilised to generate that triangle. An angle identifying this relative orientation is then stored. The processing module 42 then makes a similar determination for the relative orientations of the triangles identified by the points of the vertices projected into the image plane used for the other models and for the triangles representing those vertices in the other models.

The triangle from the mesh being processed is then deleted if either the triangle from the mesh being processed is determined to have an orientation greater than a current threshold orientation or the triangle is determined to be more oblique relative to the image planes utilised to generate the selected triangle than any of the orientations of the triangles from the other models identified by the projection of the selected triangle into the image plane utilised to generate those other models. In this embodiment the threshold value for deleting triangles is initially set at 90°. That is to say the processing module initially is arranged to delete triangles oriented at more than 90° to or away from the image plane utilised to generate a portion of the model.

If a triangle is determined to be completely represented by part of one of the other models and is determined to have been generated from data which is indicative of a more oblique angle than the threshold value or more oblique data than the data utilised to generate corresponding portions of the other models the processing module 42 then (S44) deletes that triangle from the stored model for the selected mesh.

After either triangle has been deleted or if it has been determined that a boundary triangle being considered is not represented by a portion of the other models or is not determined to have been generated utilising data indicative of a more oblique angle than the other models, the processing module 42 then (S45) determines whether all of the triangles at the edge of the mesh being processed have been considered for possible deletion.

If this is not the case, the next boundary triangle in the currently selected mesh is selected and a determination whether to delete that triangle is made (S41-S44) when all of the triangles at the boundary of one mesh have been considered the processing module 42 then (S46) determines whether all three of the wire mesh models have been considered. If this is not the case the next mesh is selected (S47) and then each of the boundary triangles at the edge of the wire mesh model represented by that mesh are individually considered for possible deletion (S41-S46).

Thus in this way each of the triangles at the edge of all three meshes are considered and where the portion of a surface represented by the boundary triangle is determined to also be represented by other data, the triangle is deleted if it has been generated from more oblique data than the other data representing that portion of the surface.

After all three of the models have been considered in turn the processing module then (S48) determines whether in the latest round of processing any triangles have been deleted from the wire mesh models.

If this is the case the processing module 42 then (S49) determines whether the current threshold value for deleting triangles is set to its maximum level. In this embodiment the maximum level is set to 75°. If the current threshold value is not set at 75° the processing module 42 then (S50) reduces the threshold by a further 5° before proceeding to select the first model for processing utilising the reduced threshold (S47).

Thus in this way the criteria for deleting triangles from the various models are gradually reduced so that initially only the more oblique triangles which are represented by more than one wire mesh are removed. As the boundary triangles are processed at each iteration, the deletion of triangles will result in additional triangles being considered for deletion. This together with the relaxation of the deletion threshold causes the processing module to gradually reduce the extent of overlap of the surfaces represented by the three wire mesh models.

If after all of the meshes have been processed utilising a particular threshold, the processing module 42 determines (S48) that no deletions have occurred in the latest round of processing or alternatively if the threshold value for deleting triangles has reached its maximum value, the processed models will comprise models where only a very small portion of the surface at the edge of one particular model is also represented by data from the other two models. The processing module 42 then (S51) proceeds to merge these minimally overlapping wire mesh models in a similar manner to that described in "Zippered Polygon Meshes from Range Images" Greg Turk and Marc Levoy, Computer Science Department, Stamford University which is hereby incorporated by reference.

In contrast to the general method described by Turk and Levoy, in this embodiment a simplified merging system is utilised. In order to increase the speed with which overlapping surfaces can be merged, the processing module 42 is arranged to consider each point at the edge of a surface in turn and identify whether the point identifies one of six different types of common overlap. If the point does not identify one of the defined types of overlap the point is deleted. If the point does identify one of the defined types the co-ordinates of the area of overlap are modified to merge the two surfaces at that point.

The result of processing surfaces in this way is to merge most of the area of overlap between a pair of surfaces. As only a limited number of types of overlap are merged, this means that the processing to achieve this merging can be performed relatively quickly as complicated cases are avoided. The gaps which result from the deletion of points can then be filled utilising calculated planes determined from the co-ordinates of the points defining the edges of the holes.

More specifically, points at the boundary of overlap between two surfaces are considered in turn. Taking one point from one surface, initially, the point is classified as to whether the point is the vertex of a single triangle or whether more than one triangle meets at that point. If the selected point is the vertex of a single triangle, the point is then classified in terms of whether the sides meeting at the vertex either overlap a single edge from the other surface, two adjacent edges on a triangle of the other surface or two other edges on the adjacent surface. In the case of a point defining the vertex of a number of triangles, a similar analysis is performed for the outer most edges of the outermost triangles meeting at the point.

After the type of overlap has been determined the two surfaces are merged. FIG. 10A is a schematic illustration of two overlapping triangles one defined by points 70, 71 and 72 and a second triangle defined by points 73,74 and 15. If point 73 were to be selected for processing initially, the processing module 42 would identify that point 73 was the vertex of a single triangle. The lines 73-74 and 73-75 would then be considered. That lines 73-74 and 73-75 overlap lines 70-72 and 72-71 would then be identified and the fact the lines 70-72, 72-71 are adjacent edges of a single triangle would then enable the type of overlap to be classified.

Figure 10B:
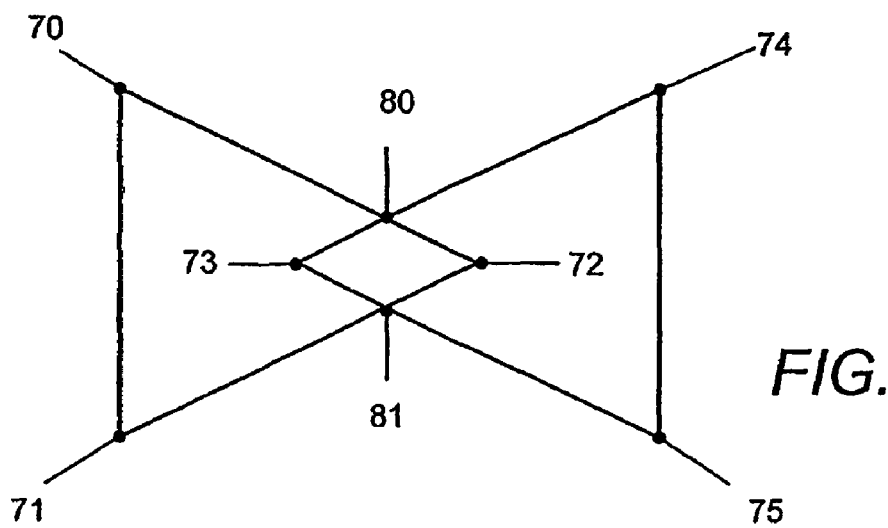

In the case of a pair of overlapping triangles such as illustrated in FIG. 10A, using conventional techniques, the closest points on lines 73-74 and 70-72 would then be identified and a new point 80 would be added at the mid point on a line connecting the two closest points. A further new point 81 is then added at the centre of a line connecting the two points on lines 73-75 and 72-71 which are closest to each other. FIG. 10B is a schematic illustration of FIG. 10A after new points 80 and 81 have been added.

Figure 10C:
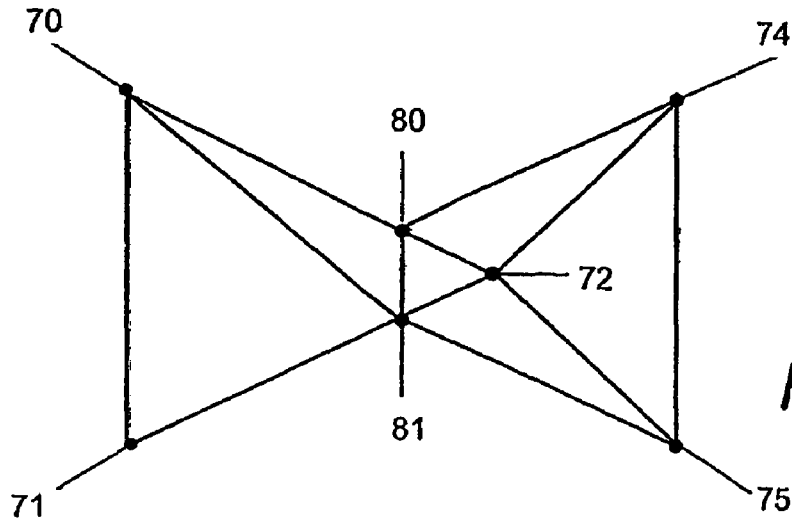

The connectivity of the meshes is then modified by replacing the connection between 73 and 74 and 70 and 72 with connections between 70 and new point 80 had between 74 and new point 80. Similarly the connections between 71 and 72 and 73 and 75 are replaced with connections between 71 and 81 and 81 and 75. Point 73 is then deleted and the polygons defined by points 72,80,74,75,81 and 70,71,81,73 and 80 are triangulated. FIG. 10C is a schematic illustration of the merged surface.

In this embodiment in addition to adding new points to the meshes defining the surfaces and deleting some points, when merging meshes, the co-ordinates of some of the remaining points are also modified.

More specifically the co-ordinates each of the points 70-72, 74,75 directly connected to the new points 80,81 are modified to account for the change in the shape of the surface arising from the replacement of the connections of these points to deleted points with the new connections to the new points. This is achieved by determining a weighted average of each point and all points connected to that point.

FIGS. 11A-E and 12A-E are schematic illustrations of the other cases processed by the processing module 42 and corresponding illustrations of the merged meshes after modification but prior to retriangulation.

More specifically, FIGS. 11A and 12A are an illustration of the processing of shared vertex 85 of a number of triangles defined by points 85-89 where the outer edges 85-86 and 85-89 overlap two adjacent edges 82-83 and 83-84 of a single triangle. As a result of processing the common vertex 85 is deleted and new points 90-93 are introduced.

In a similar way to the processing for a single triangle as has previously been described, the closest points in each overlapping line are determined and used to calculate co-ordinates for the new points 90-93. The co-ordinates for old points 82,84,86-89 directly connected to the new points 90-93 are then modified to account for the change of shape arising from the addition of the new points 90-93 in the same way as has previously been described.

FIGS. 11B and 12B are an illustration of a single triangle 94-96 having a vertex 94 which overlaps an edge 98-99 of another triangle 97-99 and the result of processing introducing new points 100,101. Again in a similar way to processing an overlapping vertex where sides of a triangle overlap two adjacent edges, in this case new points 100,101 are added at the mid point of the line connecting the closest points in the overlapping edges. The co-ordinates of adjacent points 95-99 are then modified in a similar way as has previously been described.

Figure 12C:
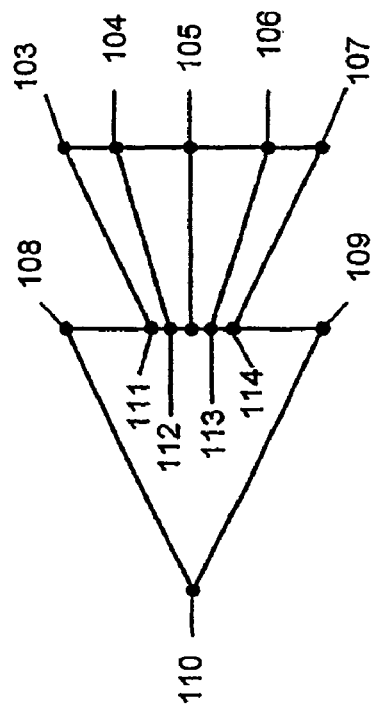
Figure 12D:
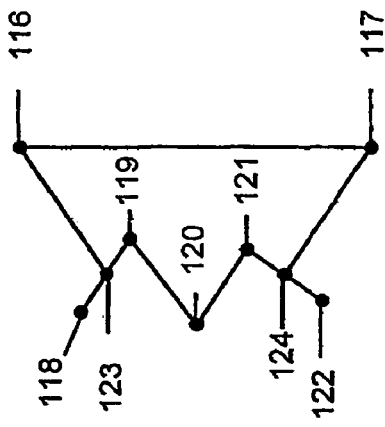
Figure 11C:
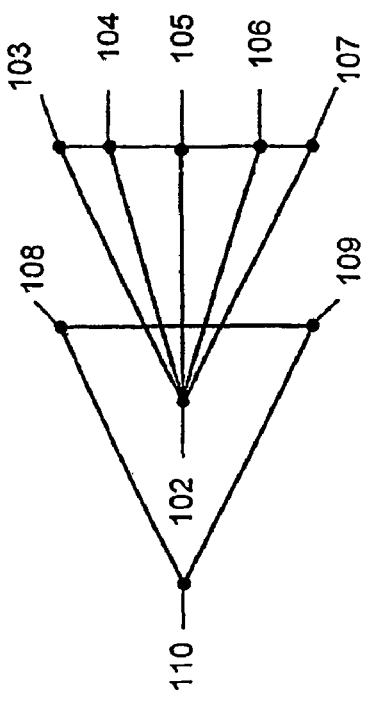
Figure 11D:
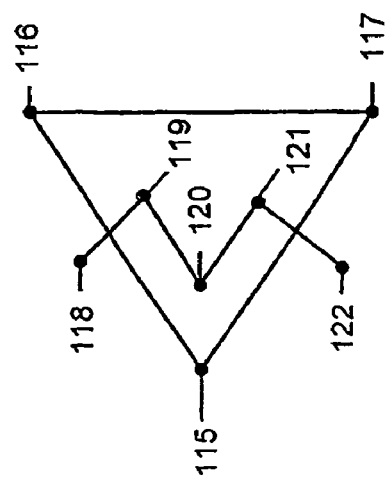
Figure 12E:
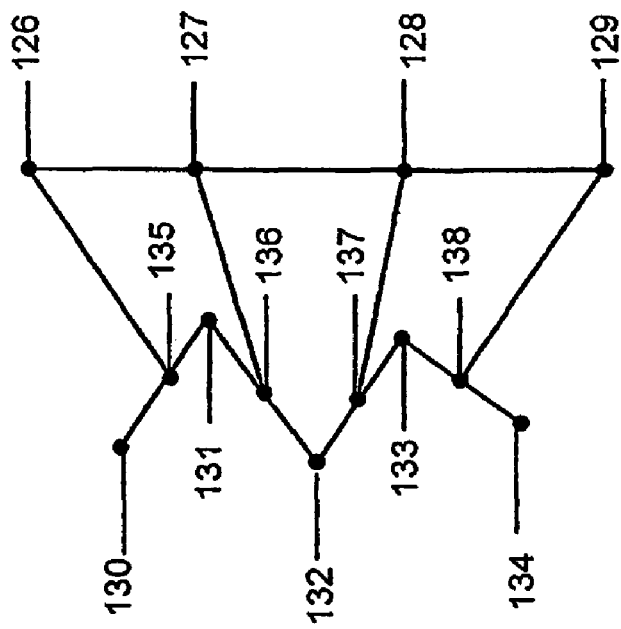
Figure 11E:
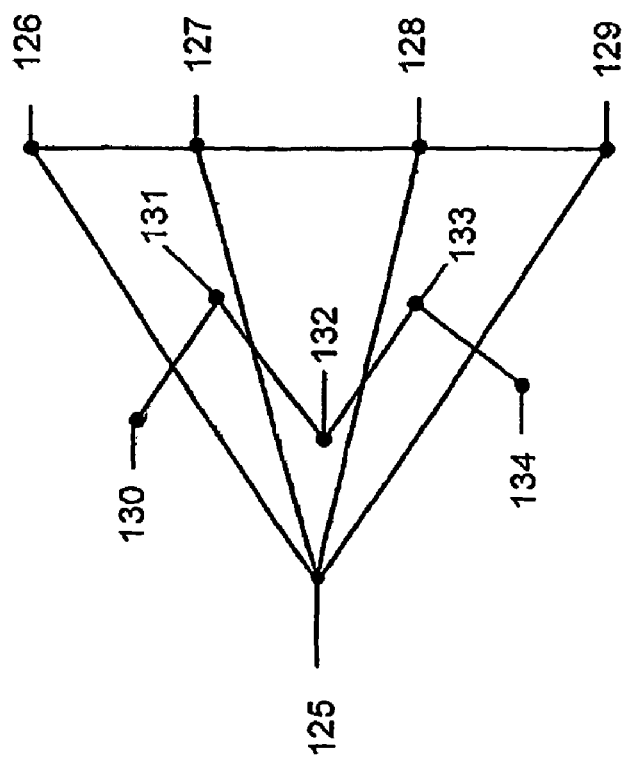

FIGS. 11C and 12C are a schematic illustration of the processing of a shared vertex 102 of a number of triangles 102-107 overlapping an edge 108-109 of a single triangle 108-110 and the results of processing in a similar manner to the example of FIGS. 11B and 12B.

Finally, FIGS. 11D and 12D and FIGS. 11E and 12E are illustrative examples of processing a triangle 115-117 and a number of triangles 125-129 which have outside edges 115-116 and 115-117 and 125-126 and 125-129 which intersect non adjacent edges of an adjacent surface 118-122, 130-134. In these cases, again new points are added at the mid points on lines connecting the closest points on pairs of overlapping edges and the connectivity of the mesh is then modified to merge the two surfaces.

After all points at the edge of the two meshes have been processed, any remaining points which do not fit into any of the above described categories are then deleted.

The result of this merging and subsequent deletion of points will mean that some holes may exist in the merged mesh. To account for this whenever a hole is encountered, which can be identified by points at the edge of either of the surfaces which are not directly connected to at least two new points, the processing module 42 then fills in the hole.

This is achieved by the processing module 42 identifying the outline of the hole and then determining the plane which fits best to the co-ordinates of the points defining outline of the hole. The normals to the plane which connects each of the points to the plane are then calculated and the co-ordinates for the points are modified by subtracting the respective calculated normal vectors so as to modify the position of the points in the outline to become points on the calculated plane. Finally a merged mesh is completed by triangulating any polygons in the defined mesh which have more than three sides.

When all three models have been processed and merged into a single model, the combined 3D wire mesh model is then utilised to generate positioning instructions to position the patient 8.

Returning to FIG. 6 when a model has been generated by the image generation module 46 the control module 44 then (S17) determines whether the instructions received from the keyboard of the computer 5 indicate that the three dimensional wire mesh model data generated by the processing module 42 is to be utilised to position the patient automatically by sending instructions to the mechanical couch 7. If this is the case the control module 44 passes data for the generated wire mesh model together with data for a stored model from an earlier treatment session retrieved from the data store 47 to the mechanical couch control module 45. The mechanical couch control module 45 then performs (S18) the automated generation of movement commands for the mechanical couch 7 in a two stage process.

Initially, the treatment couch control module 45 determines a first rough transformation for aligning the surface identified by the newly generated wire mesh model with the surface identified by the stored model. Specifically, the treatment control module 45 selects a subset of the vertices from the generated model together with a decimated wire mesh representation of the stored model. This decimated model is determined utilising conventional techniques such as are described in 'Decimation of Triangle Meshes' W. Schroeder et al Computer Graphics (SIGGRAPH '92) 26(2) pp 65-70 Aug. 1992.

For each sample vertex in the generated model, the closest vertex to the decimated stored model is determined. The closest point on the surface defined by the decimated model for the stored surface to each of the sample vertexes in the generated model is then calculated by considering each of the triangles including the identified closest vertex in the decimated model.

When determining the closest vertex from one model to that in another, a comparison of the co-ordinates of all of the vertices in second model must be made. The time necessary for such a determination is dependent upon the number of vertices in the model. Thus by decimating the stored Model using conventional techniques the numbers of vertices to be searched is reduced and hence the time taken for registration minimised. Similarly, matching a sub sample of the vertices generated model also reduces the amount of processing required.

When the closest points from the all sample vertices to the decimated surface have been determined an initial transform to align the generated surface to the decimated stored surface is calculated utilising conventional Procrustes algorithm techniques such as are described in 'Least Square Fitting of Two 3D Point Sets' Arun et al, IEEE Transactions on Pattern Analysis and Machine Intelligence Vol PAMI-9 No. 5 pp 698-700, 1987, and 'Closed Form Solution of Absolute Orientation Using Unit Quaternions' B. K. P. Horn J. Opt-Soc. Am. A. Vol 4, No. 4, pp 629-642, April 1987 both of which are hereby incorporated by reference.

The process then iterates utilising the iterated closest point (ICP) algorithm as is described in "A Method for Registration of 3-D Shapes" Paul J. Besl and Neil D McKay, IEEE Transactions on Pattern Analysis and Machine Intelligence, Vol 14, No. 2 Feb. 1992 pp 239-256, which is also hereby incorporated by reference.

After an initial rough transformation has been determined, the rough transformation is then refined by determining, for all vertices of the generated model to which the initial transformation has been applied, the closest points on the surface in the stored model.

More specifically, in this embodiment, the volume enclosing the stored surface model is divided into voxels each defining a cube in space. Every vertex in the stored model is then associated with one of the defined voxels. Data identifying which vertices are present in which voxels can therefore be prestored. In this embodiment the size of the voxels are cubes having sides selected so as to divide the longest side of a volume enclosing the stored model into 50 segments. For each voxel, a list of any vertices from the stored model present in the volume defined by the voxel is then stored.

When identifying the vertices in the stored model which are closest to vertices in the generated model, each vertex in the generated model is considered in turn. The co-ordinates of the vertex from the generated model are initially used to identify a voxel. If the identified voxel contains none of the vertices from the stored model, a larger search volume is then considered by searching the lists of vertices contained in adjacent voxels. By gradually growing the search volume in this way initial candidate closest vertices can rapidly be identified since only a small number of stored lists of vertices for the additional voxels need to be checked to see if any vertices fall within the current search volume.

Eventually a search volume including at least one candidate vertex will be identified. The distance between each candidate vertex from the stored model contained in the current search volume and the current vertex from the generated model being processed is then calculated and the closest vertex noted. The closest distance between the edge of the current search volume and the vertex from the generated model is then compared with the distance between the vertex currently being processed and the closest identified vertex from the stored model. If the distance to the closest edge of the current search volume is greater in size, the identified closest vertex is stored as the closest vertex from the stored model to the vertex currently being processed. If this is not the case a final search is conducted within adjacent voxels defining a cube having sufficient volume to enclose a sphere having a calculated radius corresponding to the distance between the vertex being processed and the identified closest vertex. The distance between the vertex currently being processed and any additional vertices from the stored model in the additional voxels in the enlarged search volume are checked to see if they are any closer to vertex being processed than the previously identified closest vertex from the stored model.

Thus in this way the closest vertices in each of the models can be determined by checking only a small number of lists associated with new voxels defining the current search volume and hence the amount of processing required is reduced. This rapid identification of the closest points is possible because the initial rough transformation for the surfaces causes the two surfaces to be relatively closely aligned and therefore causes the closest vertices to lie normally withing two or three voxels of one another. The number of voxels which need to be checked and the amount by which the search volumes need to grow before a match is found is therefore very limited.

The closest points on the surface defined by the stored model to the vertices of the generated model are then identified by considering the triangles including the identified closest vertices. Having done this for all of the vertices in the generated model, the ICP algorithm is repeated as described above to determine a final matching transformation. By utilising the entire stored and generated models to determine a matching transformation a very accurate match an be calculated. The mechanical couch control module 45 then transmits to the mechanised couch 7 instructions to orientate the couch 7 in order to account for the determined differences between the prestored model and the current generated model.

FIG. 13 is a block diagram of the control system for positioning a patient. In this embodiment, the couch control module 45 comprises a transform generator 140 for calculating a transform for matching a generated model surface with a stored surface and a control generation module 141 for generating control signals for controlling an x axis motor 150, y axis motor 151, z axis motor 152 and a rotational motor 153 respectively arranged to move the mechanical couch laterally, longitudinally, vertically and rotationally relative to the iso centre of the treatment room.

When a transform has been calculated by the transform generator 140 of the couch control module 45, the transform is then passed to the control generation module 141. The control generation module then separates the received transform into separate control signals for changing the x,y and z position of the couch and for rotating the couch. These respective control signals are sent then to each of the motors 150-153. The motors 150-153 then position the mechanical-couch to move the surface of an individual to match as closely as possible the calculated transformation.

After an initial positioning of the patient, further images of the patient are then obtained and further corrections of patient position can be made by determining the revised location of a patient and repositioning by sending the motors 150-153 further control signals based on a comparison of the stored model of the surface of the patient and a generated model of the current surface.

After any necessary movement commands have been generated and a patient positioned, the processing module 42 will continue to generate models of the surface of the patient using the latest video images received from the camera rigs 1,2,3. These models are passed to the image generation module 46 so that images of the patient can be created and displayed (S19).

Specifically when a wire mesh model is received by the image generation model 46 the image generation module 46 checks with the control module 44 for a current display status then proceeds to generate as image of the patient 8 based upon the current display status.

One possible display status in this embodiment is a status for generating a texture rendered image utilising the texture data obtained from the texture cameras 20 of the camera rigs 1, 2, 3. In such a configuration the image generation module 46 causes the frame grabber 5 to obtain image data from the texture cameras 20 of the common rigs 1,2,3. The image generation module 46 then proceeds to texture render the generated three dimensional model received from processing module 42 utilising implicit texture render coordinates from the images received the texture cameras 20 of the three camera rigs 1, 2, 3. Thus in this way an image of a patient 8 as currently viewed can be shown and displayed on the screen 11.

Alternatively in another configuration, the image generation module 46 might be arranged to generate a texture rendered image of the wire mesh model received from the processing module 42 based upon the relative differences of the positioning the surfaces of that wire mesn model relative to a previously stored wire mesh model of the patient 8 stored in the data store 47. Thus for example where the surface of the wire mesh model received from the processing unit 42 was above the corresponding portion of a surface of a stored model the surface of the model might be rendered red and where it was below the stored surface the surface might be rendered blue. Thus the image generated by the image generation module 46 would provide visual feedback to the operator to the relative positioning of the patient 8 during this and a simulation session.

Alternatively instead of a simple colour rendering of two colours, the extent to which a portion of a patient is above or below the stored surface might be indicated by the relative variation in colouring ranging from a dark colour through a light colour where the hue of the rendering indicates the relative depth of the patient relative to the stored data. In such configurations texture render data for the model would be calculated based upon a comparison of the received wire mesh model and the stored model obtained from the data store 47.

After an image has been displayed the next frame of image data is then processed and further images are generated. In this way a series of images are presented to an operator providing real time visual feedback of the position of the patient. An operator can then select appropriate times to irradiate the patient on the basis of the display.

SECOND EMBODIMENT

A second embodiment of the present invention will now be described with reference to FIG. 14. In the previous embodiment, an imaging system was described in which three camera rigs 1, 2, 3 are utilised to obtain image data of a patient 8. In this embodiment, instead of an array of cameras 18, 20, 22 on a camera rig, image data is obtained utilising a self contained camera unit. The rest of the apparatus is unmodified.

FIG. 14 is a schematic block diagram of a camera unit in accordance with this embodiment of the present invention. The camera unit comprises a set of three charged coupled devices (CCD's) 170, 171, 172. Each of the CCD's 170, 171, 172 in this embodiment comprise CCD's which do not have an asynchronous reset function. Associated with each of the CCD's 170, 171, 172 is a timer unit 180, 181,182. The timer unit 181 of one of the CCD's 171 is connected to a master timing controller 185, so that the timer unit 181 can pass a vertical reset signal (VR) to the master timing controller 185. This timer unit 181 is also connected to the timer units of 180, 182 associated with the other two CCD's 170, 172 so that the pixel clock signals (PC) for timing the duration for reading data for each pixel from the CCD's arrays can be synchronised. The master timing controller 185 is also directly connected to the two other timing units 180,182 and is also connected to a first and second flash unit 186, 187. In this embodiment, the first flash unit 186 is an ordinary flash and the second flash unit 187 is arranged to project a speckle pattern for use in matching image points.

Each of the three CCD's is also connected to a analogue digital converter 190, 191, 192 arranged to convert signals received from the respective CCD's 170, 171, 172 into a digital signal which is passed to a frame store 195. The frame store 195 comprises a latch 197 and a data store 198. The frame store 195 and the master timing controller 185 are both connected to a local area network (LAN) or other high speed interconnect so that the master timing controller 185 can receive control instructions from a controlling computer 5 and the frame store 95 can transmit image data via the LAN to the computer 5 where it is processed in a similar way to the data in the first embodiment. Additionally, the LAN provides means by which activation of three camera units can be synchronised so that as in the first embodiment simultaneous images of all sides of a patient can be obtained despite some portions of a patient being occluded in some viewpoints.

In use, when image data is to be obtained, the master timing controller 170, 171, 172 receives instructions from the LAN. These instructions indicate whether the CCD's are to be activated simultaneously or asynchronously.

If the CCD arrays are to be simultaneously activated an activation signal is automatically passed to all of the timer units 180, 181, 182 and is used to activate the first flash 186 simultaneously with the shutters of the CCD arrays 170-172. After a predetermined exposure period the shutters then close.

In order to synchronise the read out of data from the three CCD's, whenever a vertical reset signal is received by the master timing controller 185 from one of the timer units 181, the signal is automatically passed to the other two units. Due to the passing of the vertical reset signal (VR) via the master timing controller 185 the signals for each unit will not be quite simultaneous in that a very small difference in timing may occur but this difference is not significant. As the vertical reset signals (VR) and pixel clock signals (PC) used by the three CCD arrays 170-172 are identical, the A/D convertors 190-192 will read and pass to the latch 197 and datastore 198 pixel data which is synchronised and which corresponds to images obtained at the same time by all of the CCD arrays. Once a complete image has been stored in the data store 198 for all three arrays 170-172, the latch then releases the images from the data store 198 when instructed to do so by the master timing controller 185 on the basis of instructions received from the LAN.

When asynchronous data is desired, the activation signal sent by the master timing controller 185 to the two flash units 186,187 causes the first flash unit 186 to be activated shortly before the second flash 187 is activated. Simultaneously with the activation of the first flash 186, the timer unit 181 of one of the CCD's 171 causes the shutter on the associated CCD 171 array to open. Under control of the master timing controller 185, the second flash 187 is activated and the shutters of the other CCD's 170, 172 are opened for the duration of the second flash. In this embodiment the delay between the first and second flashes is made to be equal to a predetermined number of pixel clocks for example corresponding to 8 lines of read out from the CCD's 170-172. After a predetermined exposure period the shutters for all three CCD's close and image data from the CCD's are passed via their respective analogue digital converters 190, 191, to the frame store 195.

As the timer units 180-182 are synchronised, image data received via the analogue digital converters 190,192 will also be synchronised. This will mean that image data from the two CCD's activated simultaneously 170,172 will represent image data obtained from the same instant. The majority of the image data obtained from the remaining CCD will also correspond to the shutter period for the two other CCD arrays 170, 172 except that the initial portion of the data signal transmitted via the analogue digital converter 191 will correspond to part of the CCD array 171 whilst the shutter was closed. By discarding this portion of the data, three images, two slightly smaller than the other one but all of which correspond to near simultaneous exposure of the three CCD arrays 170-172 can be obtained where two images comprise images of a speckle pattern and the third does not.

When a set of three images have been stored in the frame store 195 the image data can then be transmitted via the LAN to a computer 5 for processing. As this data is already in digital form, any suitable means of transmission, such as an ethernet can be utilised to transmit this data to the computer 5. The costs of cabling are thereby reduced. Further by providing a frame store 195, which is arranged to receive image data from the three CCD's 170-172, a means for obtaining simultaneous read-out from all three cameras is provided.

Although in this second embodiment a system has been described in which image data is stored in a frame store 195 and transmitted via a LAN to a computer 5, it will be appreciated that a processing system could be incorporated within the camera unit so that a 3-D wire mesh model representing a surface could be transmitted rather than having the processing of image data occur remotely from the camera unit.

Alternative Iso Calibration System

FIG. 15 is a schematic illustration of an alternative calibration system to that described with reference to FIGS. 5A and 5B in the first embodiment. In this embodiment instead of using a cube to identify the position of the iso centre as defined by the laser projection system 9, a flat sheet 200 is provided. This flat sheet is moved from a first position 200 to a second position 202 in the vicinity of the actual iso centre 204. When in the vicinity of the iso centre the projection of laser light on to the sheet will appear as a triangle, the location and shape of which will depend upon the location and orientation of the sheet 200.

In this embodiment the variation of the triangle of laser light reflected from the sheet is utilised to determine the iso centre 204. When calibrating the system relative to the iso centre 204 images of the sheet in a first position 200 are obtained by each of the CCD arrays 170-172. The controlling computer 5 can then process each of the received images to identify within the images the triangle of laser light projected on to the sheet 200. This can be achieved by the controlling computer 5 storing an images of the triangle which results from the projection of laser light in a known position relative to the iso centre and matching the each received image from a CCD array 170-172 in the same way in which the controlling computer 5 processes and matches images to generate a surface model. In doing so, only a partial image identifying the outline of a triangle need be stored and matched.

When the location of the triangle in images of the sheet 200 in a first position have been obtained, exactly the same processing is then performed after the sheet has been moved to a second position 202. Three dimensional co-ordinates of the vertices of the projected triangles on the sheet in the first position 200 and the second position 202 can then be calculated using the obtained images. The point of intersection on lines connecting the vertices from the images of the sheet in the first position 200 and the second position 202 can then be calculated. This point will be the iso centre of the treatment apparatus 6.

Although in the previous embodiments matching of image patches has been described based solely on a transform for accounting for different relative orientations of a portion of a patient being matched, it will be appreciated that additionally, factors such as variation in relative lighting and differences in gain for different cameras or other image sensors, could also be taken into account when processing data to match patches. The processing to account for such variation would be entirely conventional.

Although in the first embodiment a system has been described in which patches are matched by recalculating iterative transforms from the difference between patch values at different iterations, it will be appreciated that transform values could be determined in a conventional way by updating both the difference matrix and the derivative matrix for patches at each iteration.

In the first embodiment, matching a generated model surface with a stored surface is described as being a two stage process. Initially a rough match is achieved utilising a decimated stored model and a sub sample of points from the generated model. An accurate match is then achieved using the rough match and a complete model of the surface. The advantage of such a system is that the decimated surface and sub sampled points can be aligned relatively quickly. A final fine match can then also be achieved quickly as since the surfaces will be already roughly aligned only relatively small search volumes need to be considered for generating the final match.

Although in the first embodiment a rough match based on decimated models is described, other methods could be used. Thus for example instead of generating an initial rough match on a decimated surface, where a greater density of points are allocated for portions of a model representative of curved surfaces a simple lower resolution subsampled triangulation of a model surface could be used to calculate the initial rough match. Although such a system would not generate quite such an accurate initial transformation, this would not matter as a final fine match could still be achieved using the full model. Using a lower resolution model would however have the advantage that the model could be more easily and therefore rapidly calculated. One way of generating such a lower resolution model would be to generate triangulation based on a sub sample of points from the original images used to generate the stored model.

Alternatively, instead of calculating an initial rough match based on a 3D model, the projection of the stored model into one of the views used to generate the current model could be used to select potential closest points for vertices in a generated model. The closest vertex from the stored model to each vertex from the current model in the image plane could then be identified by considering vertices projected to similar areas. This match could be used to identify a selection of triangles calculate a first rough transformation for matching vertices to points on the stored surface model. The advantage of such a system would be again that the initial rough transformation could be rapidly calculated.

Although in the first embodiment a system identifying the isocentre of a treatment apparatus has been described utilising a cube having a striped exterior, other systems could be utilised. An advantage of the system described in the first embodiment is that the identification of points corresponding to lines on a flat surface can be achieved relatively easily.

An alternative system could utilise a single flat plate on to which as in the previous embodiment laser cross hairs identifying the isocentre of a treatment apparatus are projected. In the case of a flat plate, the projection of three lines identifying three planes meeting at the point corresponding to the isocentre would cause three lines defining a triangle to be seen when those lines were projected onto a flat plate held obliquely close to the isocentre. The positions of three corners of the triangle could then be identified from the images obtained by the camera rigs. The ortho centre of the triangle appearing in the images can then be calculated. This is necessarily a perpendicular projection of the isocentre onto the plane where the plate was held. The distance of the plate from the isocentre can then be calculated utilising the determined distances between the points corresponding to the corners of the triangle.

Alternatively, instead of utilising the laser protector to generate an image on a flat plate, a plate having a known pattern of lines could be positioned close to a known position based on the laser light projections on to the plate. Images of the plate could then be obtained and the relative positions of the cameras could then be determined by matching the obtained images with a stored representation of the expected image of the plate at the known position.

Further images of the plate at another position could then be obtained by using the couch to move the plate by a known amount. The same detection and triangulation process would then be performed. The iso centre could then be determined utilising the calculated planes which are defined by the pattern of lines appearing in images of the plate at the two different positions and the known movement of the couch relative to the iso centre to account for the initial differences between the actual position of the plate and the position of the plate in the stored images at the expected position.

Although in the first embodiment, obliqueness of data is utilised to delete overlapping portions of models other measures of goodness of match could be used. Thus for example the path difference could be used to select triangles for deletion.

Although in the first embodiment, camera images are described as being obtained by illuminating a patient using first and second light sources 32,34 and in the second embodiment use of a first 186 and a second 187 flash is described, it will be appreciated that a combination of constant illumination and flash illumination could be used. In particular, since flash illumination can generate more consistent illumination than other light sources, a flash system could be used to generate initial models of a patient to aid in patient positioning. Since the flash illumination is largely consistent, the generated surface models should be highly accurate and therefore the patient positioning should also be accurate. Subsequently during the monitoring for patient movement, other non flash light sources could be used. Although the illumination may not be quite as accurate for the initial positioning models, the generated models would still be sufficiently accurate to monitor patient breathing and movement.

Further, although in the first embodiment the projected triangles are used to identify corresponding portions of different models, in other embodiments could use the identified triangles as a starting point for identifying exact matches for corresponding parts of models.

Additionally, the test for deleting the triangle described in the first embodiment could be amended for example all triangles covered by others which are oriented at an angle greater than a threshold could be deleted. Alternatively, triangles could be required to be both above a threshold and worse than the corresponding triangles in order to be deleted.

Although in the previous embodiments systems have been described in which image processing of stereo images is utilised to generate models for positioning a mechanical couch, it will be appreciated that the processing system described has wider applicability.

In the radiotherapy field, in addition to generating positioning instructions, the data obtained could be utilised in a number of other ways. For example the detailed three-dimensional models could be utilised to perform contouring to help in the calculation of a treatment plan. As the generated contours will be based upon the accurate measurements obtained from the camera rigs 1, 2, 3. The resulting contours will be highly accurate so that an optimum treatment plan can be determined.

Alternatively, the models could be utilised to activate the treatment apparatus automatically so that for example the breathing cycle of a patient could be monitored and the application of radiotherapy applied at the same point during the breathing cycle when the patient was closest to a planned treatment position. In such a system, the wire mesh model data generated would be utilised to control the treatment apparatus gating so that the synchronisation of treatment and the breathing cycle could be achieved.

Further instead of matching the position of the patient so that treatment and planning are achieved with the patient in the same orientation, the present invention could be utilised to determine the differences in position of the patient so that diagnostic data such as Magnetic Resonance Imaging (MRI) or X-ray CT data from the same patient could be aligned with one another even when the patient was not in exactly position when different data types were obtained.

An additional use of the data identifying a patient's position would be in the control of the movement of the treatment apparatus so that collision between the apparatus and any portion of a patient's body could be avoided.

The invention is equally applicable to other applications where the fast generation of a three-dimensional model of an individual from camera images is desirable. In view of the speed of which models can be generated utilising the present invention, the present invention is particularly applicable for obtaining three-dimensional models of a moving individual to identify for example muscular problems in physiology or sports imaging.

The present invention also has applications outside of the medical field for example in body scanning for clothes or machine vision more generally where three-dimensional monitoring of products, for example, production lines is desired. The modelling systems could also be utilised to obtain data for giving motion capture for generation of animation or alternatively for security applications matching the shape of individuals to confirm identity. In security systems the modelling unit could be arranged to monitor the content of images and model faces of detected individuals whenever a face was detected in received images.

In the above described embodiments, a 3D model of a surface is generated by matching corresponding patches in a pair of images of a speckle pattern projected onto the surface being modelled. In order to generate an accurate model, it is important to obtain images where the speckle pattern being matched is clearly discernable. This can be achieved by manually adjusting the gain and exposure until well contrasted images are obtained. Alternatively, the system could be arranged to automatically calibrate gain and exposure.

In such a system a light meter could be arranged to obtain light readings whilst images of a test object were obtained. The gain and exposure settings could then be set automatically. Alternatively, gain settings could be adjusted based on the extent of saturation level pixels in images in a feedback loop when a test object was viewed by the cameras. For example, the setting could be automatically adjusted until no more than a threshold percentage of pixels in an image were saturated black or saturated white. In this way, the gain and exposure settings could be selected so as to ensure that a projected speckle pattern was discernible in the images.

An additional problem encountered when obtaining actual images of patients is that images of the protected speckle pattern are affected by the patient's skin colour. That is to say lighter, and sweaty and therefore shiny skin reflects more light than darker drier skin. In order to account for such variation, gain and exposure settings could be reset for each individual patient based on images of the speckle pattern projected on to that patient. Alternatively, settings for a variety of skin colours and types could be prestored and appropriate settings selected for each patient.

Although in the second embodiment a system has been described in which a single master clock is used within each camera rig, it will be appreciated that the clocks for different camera rigs could be run using a single master clock. Thus for example in the case of three camera rigs, one camera rig could be as described in the second embodiment, whereas the two other rigs could be clocked using a signal from the first rig. Such a system would have the advantage that the images obtained from different rigs would be substantially synchronised. The model generated by merging the models generated by the different camera rigs would therefore represent the surface of a patient at the same point in time.

When initially positioning a patient, it is preferable to generate and utilise very high resolution images and models so that the initial patient positioning is very accurate. When subsequently monitoring a patient's movement, utilising very high resolution images and models can result in the time lay between obtaining images and generating a model which is unacceptable. In order to reduce the time lag lower resolution images and models could be used. Thus for example instead of processing every pixel in an image models could be generated utilising only a subset of the available pixels.

One important factor in the time lag between obtaining an image and generating a model is the frame rate at which images are obtained and read out from the cameras. In order to increase the frame rate when monitoring patient movement, the effective frame rate can be increased by utilising a camera draft mode where only part of an image is read out for a frame. Such a draft mode might involve only reading out data from a central portion of a camera image or alternatively only reading out for example every third line of an image.

In the current application, where most patient movement normally arises due to a patient's breathing cycle utilising the central portion of a rectangular image is a preferable way of increasing frame rate. This is because the central band halfway down the short side of a rectangular image is the portion of an image which can be used to obtain the greatest amount of depth information for modelling a patient's breathing. In other applications where a wider field of view is required reading and utilising a selection of lines from throughout an image may be preferable.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. An apparatus for combining two wire mesh models comprising:
   a model store configured to store model data representative of three dimensional co-ordinates of a first and second wire mesh model of a surface;
   an overlap identifier operable to identify portions of wire mesh models stored in said model store representative of the same portions of a surface; and
   a processing module operable to:
      delete from first and second wire mesh models stored in said model store model data representative of vertices of the boundary of one said models where triangles including said vertices are completely represented in part of said other model;

classify vertices at the boundary of a model on the basis of whether said vertices define part of one or more triangles and the number of edges the triangle defines by said vertices overlap;

generate new co-ordinates for shared points on the boundary between said models on the basis of the classification of said vertices; and delete said classified vertices, wherein said processing module is operable to generate new co-ordinates only when a co-ordinate is classified as defining a vertex of one or more triangles where the edges of individual triangles only overlap a single edge of triangles defined in said other model.

2. The apparatus of claim 1, wherein said processing module is operable to modify the co-ordinate data of points defining the outline of holes in said combined wire mesh models by:

determining a best fit plane for points defining the outline of a hole; and modifying said co-ordinate data for said points so as to cause said points to be represented by co-ordinates of points lying within said plane.

3. A method of combining two wire mesh models comprising:

storing model data representative of three dimensional co-ordinates of a first and second wire mesh model of a surface;

identifying portions of stored wire mesh models representative of the same portions of a surface;

deleting from said stored first and second wire mesh models model data representative of vertices of the boundary of one said models where triangles including said vertices are completely represented in part of said other model;

classifying vertices at the boundary of a model on the basis of whether said vertices define part of one or more triangles and the number of edges the triangle defines by said vertices overlap;

generating new co-ordinates for shared points on the boundary between said models on the basis of the classification of said vertices; and deleting said classified vertices, wherein the generating new co-ordinates occurs only when a co-ordinate is classified as defining a vertex of one or more triangles where the edges of individual triangles only overlap a single edge of triangles defined in said other model.

4. The method of claim 3, further comprising modifying the co-ordinate data of points defining the outline of holes in said combined wire mesh models by:

determining a best fit plane for points defining the outline of a hole; and modifying said co-ordinate data for said points so as to cause said points to be represented by co-ordinates of points lying within said plane.

5. A non-transient computer readable medium storing computer implementable instructions which when interpreted by a programmable computer cause the computer to:

store model data representative of three dimensional co-ordinates of a first and second wire mesh model of a surface;

identify portions of stored wire mesh models representative of the same portions of a surface;

delete from said stored first and second wire mesh models model data representative of vertices of the boundary of one said models where triangles including said vertices are completely represented in part of said other model;

classify vertices at the boundary of a model on the basis of whether said vertices define part of one or more triangles and the number of edges the triangle defines by said vertices overlap;

generate new co-ordinates for shared points on the boundary between said models on the basis of the classification of said vertices; and delete said classified vertices, wherein the computer implementable instructions are such to cause a computer to generate new co-ordinates only when a co-ordinate is classified as defining a vertex of one or more triangles where the edges of individual triangles only overlap a single edge of triangles defined in said other model.

6. The computer readable medium of claim 5, wherein the computer implementable instructions are such to cause a computer to modify the co-ordinate data of points defining the outline of holes in said combined wire mesh models by:

determining a best fit plane for points defining the outline of a hole; and modifying said co-ordinate data for said points so as to cause said points to be represented by co-ordinates of points lying within said plane.

* * * * *